United States Patent [19]
Hayes

[11] Patent Number: 6,165,217
[45] Date of Patent: Dec. 26, 2000

[54] SELF-COHERING, CONTINUOUS FILAMENT NON-WOVEN WEBS

[75] Inventor: Byron K. Hayes, Flagstaff, Ariz.

[73] Assignee: Gore Enterprise Holdings, Inc., Newark, Del.

[21] Appl. No.: 08/942,371

[22] Filed: Oct. 2, 1997

[51] Int. Cl.[7] .................................. A61F 2/02; A61K 9/70; B32B 5/12; C08L 69/00
[52] U.S. Cl. ...................................... 623/11.11; 623/23.58; 428/36.4; 428/36.5; 428/296; 528/354; 525/413; 602/46
[58] Field of Search ...................... 623/11, 11.11, 623/23.58; 428/36.4, 36.5, 296; 602/46; 528/354; 525/413

[56] References Cited

U.S. PATENT DOCUMENTS

| | | | |
|---|---|---|---|
| 3,839,297 | 10/1974 | Wasserman et al. | 260/78.3 |
| 3,875,937 | 4/1975 | Schmitt et al. | 128/156 |
| 3,977,440 | 8/1976 | Phillippi | 138/125 |
| 4,053,442 | 10/1977 | Jungr et al. | 260/29.6 |
| 4,137,921 | 2/1979 | Okuzumi et al. | 128/335.5 |
| 4,163,819 | 8/1979 | Yung et al. | 428/198 |
| 4,211,689 | 7/1980 | Borman | 260/40 |
| 4,243,775 | 1/1981 | Rosensaft et al. | 525/415 |
| 4,300,565 | 11/1981 | Rosensaft et al. | 128/335.5 |
| 4,429,080 | 1/1984 | Casey et al. | 525/415 |
| 4,474,630 | 10/1984 | Planck et al. | 156/62.4 |
| 4,910,064 | 3/1990 | Sabee | 428/113 |
| 4,916,193 | 4/1990 | Tang et al. | 525/413 |
| 4,920,203 | 4/1990 | Tang et al. | 525/409 |
| 5,080,665 | 1/1992 | Jarrett et al. | 606/219 |
| 5,252,701 | 10/1993 | Jarrett et al. . | |
| 5,393,594 | 2/1995 | Koyfman et al. | 428/224 |
| 5,415,779 | 5/1995 | Markell et al. | 210/635 |
| 5,433,909 | 7/1995 | Martakos et al. | 264/209.1 |
| 5,466,517 | 11/1995 | Eschwey et al. | 428/288 |
| 5,470,639 | 11/1995 | Gessner et al. | 428/152 |
| 5,505,952 | 4/1996 | Jiang et al. | 424/423 |
| 5,514,378 | 5/1996 | Mikos et al. | 424/425 |
| 5,575,874 | 11/1996 | Griesbach, III et al. | 156/167 |
| 5,582,907 | 12/1996 | Pall | 428/287 |
| 5,656,205 | 8/1997 | Rabolt et al. . | |
| 5,674,286 | 10/1997 | D'Alessio et al. | 623/11 |
| 5,681,873 | 10/1997 | Norton et al. | 523/115 |
| 5,851,229 | 12/1998 | Lentz et al. | 623/1 |

FOREIGN PATENT DOCUMENTS

| | | |
|---|---|---|
| 19641334 | 4/1998 | Germany . |
| 9210218 | 6/1992 | WIPO . |
| 9732616 | 9/1997 | WIPO . |

OTHER PUBLICATIONS

Bates FS. Polymer–Polymer Phase Behavior. Science 1991, 251:898–905.

Bates FS. Block Copolymer Thermodynamics: Theory and Experiment. Annu Rev Phys Chem 1990; 41:525–57.

(List continued on next page.)

*Primary Examiner*—V Millin
*Assistant Examiner*—Choon P. Koh
*Attorney, Agent, or Firm*—Wayne D House

[57] ABSTRACT

A web of continuous filaments which are made of at least one semi-crystalline polymeric component covalently bonded as a linear block copolymer with or blended with one or more semi-crystalline or amorphous polymeric components. The filaments are intermingled together to form a porous web of filaments, the filaments having multiple contact points with each other within the web. The filaments are bonded at the contact points without requisite for added adhesive binders, adjuncts or post extrusion melt processing. The web may be bioresorbable. The web may also be provided in forms with relatively high cohesive shear strength. The polymeric components of the filaments exist, at least temporarily, in a homogenous substantially phase miscible uncrystallized state. If preserved in the homogenous substantially phase miscible uncrystallized state, the object can then be manipulated into a distinct desirable molded shape and then subsequently set or crystallized to retain the desired form particularly suitable for a specific use or application.

42 Claims, 2 Drawing Sheets

OTHER PUBLICATIONS

Brinen JS et al. The Effect of Polymer Architecture on the SIMS Spectra of Glycolide/Trimethylene Carbonate Copolymers. Surface and Interface Analysis 1993, 20:1055–1060.

Brinen JS et al. XPS and SIMS Studies of Biodegradable Suture Materials. Surface and Interface Analysis 1991, 17:259–266.

Cha Y and Pitt CG. The biodegradability of polyester blends. Biomaterials 1990; vol. 11 Mar., 108–112.

Clark JN et al. Re–examination of poly(methylmethacrylate)/poly(epichlorohydrin) blends by small angle neutron scattering and differential scanning calorimetry. Polymer 1992; 33:3137–44.

Desai AB and Wilkes GL. Solvent–Induced Crystallization of Polyethylene Terephthalate. J Polymer Sci 1974, 46:291–319.

Engelberg I, Kohn J. Physico–mechanical properties of degradable polymers used in medical applications: a comparative study. Biomaterials 1991, 12:292–304.

Fernandes AC, Barlow JW, Paul DR. Aliphatic Polyester Miscibility with Polyepichlorohydrin. J Applied Polymer Sci 1984, 29:1971–83.

Hutmacher MS et al. A Review of Material Properties of Biodegradable and Bioresorbable Polymers and Devices for GTR and GBR Application. Intl J of Oral & Maxillofacial Implants, Nov. 5, 1996:667–678.

Khan AYA et al. Polymer–Laid Nonwovens From Poly(Lactide) Resin. International Nonwovens Journal; Jul. 2, 1995:26–73.

Lin HL et al. Hydrolytic degradation and morphologic study of poly–p–dioxanone. J Biomedical Materials Research 1993, 27:153–166.

Li W and Prud'Homme RE. A Study of Phase Separation of Crystalline and Miscible Polymer Blends. Poly(e–caprolactone)/poly(styrene–co–Acrylonitrile). J Polymer Science 1993, 32:719–727.

Luyten MC et al. Morphology in binary blends of poly(vinyl methyl ether) and e–caprolactone–trimethylene carbonate diblock copolymer. Polymer 1997, 38:509–519.

Pizzoli M et al. Crystallization Kinetics and Morphology of Poly(3–hydroxybutyrate)/Cellulose Ester Blends. Macromolecules 1994, 27:4755–4761.

Rocha G and McCarthy S. Polymers in Biodegradable Surgical Devices: Blending Poly(glycolic–acid) with Other Biodegradable Plastics. Medical Plastics and Biomaterials 1996, 44–48.

Sandberg E et al. Bone Regeneration by the Osteopromotion Technique Using Bioabsorbable Membranes: An Experimental Study in Rats. J Oral Maxillofac Surg 1993, 51:1106–1114.

Shonaike GO. Studies on Miscibility of Glass Fibre Reinforced Blends of Polyethylene Terephthalate With Polybutylene Terephthalate. Polym Journal 1992, 28:171–181.

Song M et al. Modulated differential scanning calorimetry: 4. Miscibility and glass transition behaviour in poly(methylmethacrylate) and poly(epichlorohydrin) blends. Polymer 1996; 25:5661–5665.

Vaughn EA. Nonwoven Fabric Primer and Reference Sampler. INDA Association of the Nonwoven Fabrics Industry 1992.

Wadsworth LC and Goswami BC. Nonwoven Fabrics: Spunbonded and Meltblown Processes. $8^{th}$ Annual Nonwovens Workshop Jul. 1990.

Xing P et al. Miscibility and Crystallization of Poly($\beta$–hydroxybutyrate) and Poly(p–vinylphenol) Blends. Macromolecules 1997, 30:2726–2733.

Zellin G et al. Healing of mandibular defects with different biodegradable and non–biodegradable membranes: an experimental study in rats. Biomaterials 1995, 16:601–609.

INDA Standard Test: IST 90.2(95). Standard Test Method For Stiffness of Nonwoven Fabrics Using The Gurley Tester. Association of the Nonwoven Fabrics Industry 1995.

ASTM Designation D 3164–92a. Standard Test Method For Strength Properties of Adhesively Bonded Plastic Lap–Shear Sandwich Joints in Shear by Tension Loading. Annual Book of ASTM Standards Dec. 1992, vol. 15.06.

SELF-COHERING, CONTINUOUS FILAMENT NON-WOVEN WEBS

FIELD OF THE INVENTION

This invention relates to continuous filament non-woven structures fabricated from semi-crystalline polymeric materials. More particularly the invention relates to said structures that are self-cohering webs fabricated from bioresorbable polymeric materials which are found useful as surgical implants.

BACKGROUND OF THE INVENTION

This invention relates to compositions that are useful in medical applications intended to provide for integration with and subsequent attachment to the surrounding mammalian tissue. A requirement for any medical device that is to become well integrated with the surrounding host tissue is an open structure on the surface of the implant that is sufficiently large for cells to readily penetrate. If the open structure is sufficiently large to allow for the ingrowth of both collagenous and vascular tissues, a well tolerated attachment between the implant and the surrounding tissue is then possible.

Porous structures for implantable devices sufficiently large to allow ingrowth and attachment of tissue can be achieved through a variety of means. Various technologies are able to deliver tailored open-celled structures with various pore sizes to fit the particular cell ingrowth applications. Use of expanded polymeric membrane materials, such as expanded polytetrafluoroethylene (e-PTFE) is one such technique. It can be tailored to provide optimal tissue integration. It is considered chemically inert and therefore possesses enhanced biocompatibility.

The use of extruded fibers or filaments and their subsequent assembly into a variety of organized structures is common. These structures fall into the categories of traditional weaving and knitting. Such weave and knit technologies can be found in various "meshes" found under the trade names of Vicryl®, Dexon®, and Proline® meshes. The resulting structural integrity is primarily due to the alignment of the component fibers into bundles, which are then weaved or knitted into the particular desired construction. Besides the high cost and complexity of the knitting and weaving equipment, a particular additional drawback of such construction is an increased potential for colonization and wicking of bacteria within the interstices of the aligned fiber bundles if the implant becomes contaminated.

Another method of assembling fibers is as a non-woven fibrous construction. This construction involves a random arrangement of fibers or filaments rather than the organized fibrous construction which typifies weaves and knits. The random nature of the non-wovens structure makes manufacturing of the fabric easier than weaves and knits. However, few fibrous implants utilize non-woven constructions since the mechanical interlocking between fibers in such webs are generally weak. Consequently only limited applications such as felts and pledgets exist for the non-woven implantables that are dependent on fiber entanglement for their mechanical integrity; these possess relatively poor cohesive or tensile strength. Non-woven strength can be added by the addition of a subsequent binding process which produces an attachment of the randomly deposited fibers at their points of contact. One of the few non-woven implantables on the market is Resolut® Regenerative Material which is disclosed in PCT #WO92/10218 and is composed of staple fibers and an adhesive binder to produce its bioresorbable non-woven structure.

Bioresorbable materials are particularly desirable for use in many medical applications, especially in implant applications, controlled release, and cell growth tissue engineering applications. Most implantable bioresorbable materials are used either in the form of sutures or in the controlled delivery of drugs or other bioactive agents. In the case of sutures or other structures which bear mechanical loads during at least part of their implantation, semi-crystalline polymer systems are utilized. Conversely, controlled release applications where no mechanical loading is required typically utilize amorphous polymer systems for their consistent diffusion properties.

A useful implant application for a non-woven construction is as a barrier material in mammalian tissue regeneration, also known as guided tissue regeneration (GTR). In one such GTR application, either a non-resorbable or bioresorbable membrane can be employed to separate an area where bone growth is desirable from adjacent areas where competing faster growing gingival tissue may be present. The implanted GTR membrane is used as a protective cover and acts as a barrier to entry by the other tissues into the space where bone growth is desired. Simultaneously the barrier must also resist collapsing into the defect under the pressure of the overlying tissues. The advantage of a bioresorbable material is that once its primary purpose is achieved it will be absorbed, thus eliminating any surgical need to remove it.

The preservation of space between the surface of the defect and the desired contours of the subsequently regenerated surface is necessary in order to allow for the regeneration of tissues into that space. Periodontal structures which may be regenerated in this fashion are the periodontal ligament, bone and cementum. The barrier material allows propagation of bone and periodontal ligament cells by precluding entry of epithelial cells and gingival connective tissue cells into the provided space.

One commercially available material that provides a cell-barrier for periodontal guided tissue regeneration is GORE-TEX® Periodontal Material. This is an expanded polytetrafluoroethylene (e-PTFE) material that serves as a cell-barrier between the gingiva and a periodontal defect and is intended to preserve the necessary space between the surface of the defect and the desired contours of the subsequently regenerated surface. This material is made of porous expanded PTFE having a microstructure of nodes interconnected by fine fibrils. One portion of the total surface area of the GORE-TEX Periodontal Material has a porous structural surface that becomes infiltrated with blood clot and ingrown with fibrous connective tissue, thereby inhibiting epithelial migration. The remaining portion of the surface area has a cell-barrier structure of low porosity for isolating the overlying gingival connective tissue from the underlying defect. It is not bioresorbable, however, and must be removed in a subsequent surgical procedure.

Another commercially available cell barrier sheet material intended for guided tissue regeneration is the previously mentioned Resolut® Regenerative Material, also from W. L. Gore & Associates, Inc. PCT application #WO92/10218 describes this material as a bioabsorbable material made of a non-woven fibrous matrix of polyglycolic acid fibers laminarly affixed to a cell-barrier sheet material that is a copolymer of polylactic acid and polyglycolic acid. The overall material is intended to provide sufficient rigidity in vivo to maintain space over the defect as it regenerates.

There have been other attempts to produce suitable surgical barriers from bioresorbable materials. A 70 micron thick solvent-cast bioresorbable polylactic acid membrane having no inherent porosity or tissue cell permeability was tested in periodontal applications as a cell-barrier material for exclusion of epithelium and gingival connective tissue during healing (I. Magnusson, et al., "New Attachment Formations Following Controlled Tissue Regeneration Using Biodegradable Membranes", J. Periodontal, January 1988, pp. 1–6). Tests showed some new formation of cementum and bone. Reproductions of this material demonstrated poor surgical handling characteristics due to its thin friable construction and also proved to be difficult to suture because of its brittleness. This material makes no provision for tissue ingrowth on either of its surfaces.

Another commercially available material for use in guided or controlled tissue regeneration is Vicryl® Periodontal Mesh available from Johnson & Johnson. The Vicryl Periodontal Mesh is comprised of woven fibers made from a bioresorbable copolymer of about 90% glycolide and 10% lactide. Studies have shown that the Vicryl Periodontal Mesh has had some success as a barrier material that provides for tissue regeneration (Fleisher, et al., "Regeneration of Lost Attachment Apparatus in the Dog Using Vicryl Absorbable Mesh", International Journal of Periodontics and Restorative Dentistry, 2/1988, pp. 45–55). This material is a single layer material of woven construction that is intended to both promote tissue ingrowth and simultaneously serve as a tissue barrier. As these are somewhat contradictory objectives for a single layer material of woven construction having a degree of inherent porosity, ingrowth can only be made to occur at the expense of the barrier function. The effectiveness of this material is therefore a compromise between the material's ability to allow for tissue ingrowth and the requirement to simultaneously function as a tissue barrier. An additional difficulty with this conventional woven construction is its lack of adequate rigidity and a resulting inferior ability to maintain space adjacent to the defect.

While most of the preceding guided tissue regeneration bioresorbable designs utilize readily available polymers and copolymers derived from glycolic and lactic acids, a particular polymer which provides both sufficient in vivo rigidity and longevity to resist its collapse into a defect is described in U.S. Pat. No. 4,243,775 to Rosensaft, et al and in U.S. Pat. No. 4,300,565. The disclosed material is a block copolymer of glycolide (PGA) and either lactide (PLA) or trimethylene carbonate (TMC) that is described as useful for absorbable articles such as sutures. The specific block copolymer combination of PGA:TMC has been used extensively as commercially available surgical sutures produced and marketed by Davis & Geck under the trade name of Maxon®. This same polymer system has been utilized to produce a non-porous structure for the repair and regeneration of bone that is disclosed in U.S. Pat. No. 5,080,655 issued to Jarret, et al. The disclosure describes an absorbable deformable surgical device fabricated from the same PGA:TMC copolymers described within Rosensaft (U.S. Pat. No. 4,243,775) and Casey (U.S. Pat. No. 4,429,080). None of these refer to embodiments that can be described as non-woven fibrous structures. Other bioresorbable block copolymer systems which are of potential relevance to this invention are described within U.S. Pat. No. 4,916,193 and U.S. Pat. No. 4,920,203.

Besides planar porous materials, it is additionally desirable in some implantable applications to deliver a porous three dimensional object for the function of filling a particular space, rather than for covering it as has been described above. Filling of a defect with a porous biomaterial is a common approach toward treating bone defects. In such applications open celled bioresorbable foams are common, however these materials generally possess limited tensile strength since it is relatively difficult to introduce molecular alignment, also known as molecular orientation, into such a structure. Conversely, numerous methods exist for inducing molecular orientation and thereby enhanced strength into fibrous or expanded node and fibril structures. However, three dimensional fibrous webs cannot be readily produced without the use of either adhesives, adhesive adjuncts, or compression, two of which are processes which inherently reduces the loft of the web leading to more web density and a consequential reduction in the potential for tissue integration. Besides introducing an ongoing risk of dissimilar degradation profiles, the use of an additional adhesive to bond between the web's filaments leads to more material present within the web resulting in decreased void space and an increased mass that delivers the expectation of a proportionally more reactive tissue response upon bioresorption.

The construction of a single component non-woven web without the use of binders is commonly achieved through the direct application of heat and pressure to create a localized melting or fusion of the web filaments at fiber crossover points. However, since heating fibers in the solid state can deliver only limited melt viscosity to the bonding interface without damaging overall fiber integrity, such an approach commonly delivers relatively weak inter-fiber attachments when compared with webs utilizing adhesive binders. Also, regardless to the quality of the produced inter-fiber bonds, such compression under heat inherently reduces web loft, therefore increasing the web's apparent or overall density and limiting the relative amount of available open space within the web for tissue ingrowth.

There remains a need for a non-woven implantable bioresorbable material that is composed of a structure formed from a sufficiently homogenous underlying construction that it would provide for bioresorption in a consistent structural manner as the implant degrades. However, current non-woven fabrics, especially those constructed from bioresorbable polymers, do not meet this need. Fibers in web form are typically bonded together at their points of contact by the application of various known binders or binding techniques, many of which also include the application of pressure which in turn reduces the available loft. Further, with increased concentration of binders, fabrics tend to be stiffer.

The use of any external binder also introduces issues of the uniformity of its distribution throughout the web. Additionally, the properties of the entire web become limited to the properties of the binder which gives the web its integrity, also referred to as cohesion. Thus, for example, if a binder with a relatively low melting point is used as a bonding material, the temperature conditions to which the web may be subjected are limited by the melting point of the binder. Additionally, if the binder is weakened or softened by other factors such as moisture, solvents, or various physiological fluids, then the overall integrity of the web can be affected. These problems are overcome by the self-cohering properties of the present invention.

Solvent bonding, where the reinforcing fibers are swelled by solvent in either liquid or vapor form to provide bonding of the web, is not easily controlled and frequently tends to weaken the web's fibers. Furthermore, the intersections at which the filaments are bonded frequently have a swollen appearance and possess alteration of their polymeric organization or crystalline structure with a resulting loss in strength.

Solvent spinning or "dryspinning" is a process where a polymeric material is dissolved within a suitable solvent to produce a viscous solution which is then extruded through a spinnerette. This process has been used to form non-woven webs with filaments which self-adhere at points of contact due to the use of the solvent as a tackifier adhesive adjunct. When the exiting fluid is directed at a rotating mandrel, non-woven tubular constructions are possible and have been utilized as an implantable vascular graft such as the Vascugraft® polyesterurethane vascular prosthesis manufactured by B. Braun Melsungen AG (Melsungen, Germany). Other descriptions of this or similar solvent spinning processes used to form non-woven medical implants can be found in U.S. Pat. Nos. 4,323,525 and 4,474,630.

Since the utilized solvent essentially plasticizes or lubricates the polymer chains to the point of dissolution, its removal to a concentration level where its presence no longer significantly affects the polymer's physical properties becomes essential. Such a removal process, typically evaporation by heat, constitutes an additional processing step which becomes more difficult to complete as the acceptable or tolerable residual solvent level becomes lower. This residual level of solvent, which in all cases is detectable at some level, carries particular significance in implantable applications where, dependent on the toxicity of the included solvent, its presence may cause a detrimental bioresponse as it diffuses from an implant. This is of a particular concern in with bioresorbable polymers where the produced implant degrades completely and, in many cases, the only solvents which dissolve the polymer are especially toxic. This is particularly the case with hexafluoroisopropanol and the other similarly toxic fluorinated chemicals that are required to dissolve either PGA homopolymers or PGA block copolymers.

Webs can be produced by melt-blowing or spun-bonding. Meltblown webs are produced by entraining melt spun fibers with convergent streams of heated air to produce extremely fine filaments. Melt blown processing has commonly been described as forming discontinuous sub-denier fibers, relatively short filaments that are typically 1 micron or less in diameter. Since melt blown fibers attain their final diameter while in a semi-molten state, no method is available to further enhance molecular orientation within the fibers before they cohesively attach to each other as a web on the collector screen. The net result is a web of short fibers with low to moderate strength when compared with other fibrous non-woven constructions.

Fabrication of the fibers of spunbond non-wovens is accomplished through entrainment of melt spun fibers followed by subsequent cooling and attenuation utilizing air or mechanical methods to induce molecular orientation or alignment into the resulting continuous filaments. The resulting fibers are generally in the range of 15 micron to 25 micron in diameter. Consequently, spunbond webs are made of continuous fibers or filaments that are generally greater than 10 micron in median diameter. Spunbond processes, however, are generally recognized as requiring a separate bonding step (thus the term spunbond) which interlocks the heretofore unattached fibers. Methods of spunbond interlocking generally utilize either thermal fusion, mechanical entanglement, chemical binders or adhesives, or combinations thereof. However the continuous layering of the drawn spunbond fibers on top of one another causes the surface layer of fibers to have limited integration with lower layers, resulting in an increased ability for the web to lose fibers or fray if the interfiber adhesion is overcome. It is common to compensate for this low web cohesive strength by thermally fusing the web's fibers at intermittent points. However, this heat and pressure process, known as point bonding or thermofusion, virtually eliminates web porosity within the fused areas.

An autogenous self-bonding web made without any requirement for ensuing compression is described in Yung U.S. Pat. No. 4,163,819. The self-cohering properties of the fibers of the produced web are described as being dependent on reduced crystallization dependent on the presence of a polyhydric alcohol (polyol) sequence contained in a block terpolymer. Such polyols are known to readily hydrate and the disclosure describes prevention of crystallization and the enhancement of fiber tackiness when the polymer system is exposed to water. No provision was made for autogenous self-bonding or self-cohering non-woven webs from polymer systems that could not be classified as polyols. Neither the polymers that were utilized nor the produced articles were described as being useful in an implantable application, nor is the utilized polymer systems considered as bioresorbable. Also, no description of enhanced cohesive or peel strength within the produced web could be identified.

Eschewy, U.S. Pat. No. 5,466,517 assigned to Freudenberg, describes a self bonding web made from biodegradable polycaprolactone homopolymer and blends. Biodegradable in this patent is meant to be degradable by bacteria and microorganisms in soil. The webs described were self cohering and possessed an area density of less than 120 g/m$^2$. Such a low web density with this particular polymer is likely to result in a web with relatively low tensile and cohesive strength, values not reported within the disclosure. Additionally, the 40–50° C. heated air used in producing the described self-bonding web remains sufficiently close to the 60° C. melting point of the polycaprolactone homopolymer that interfiber attachment or bonding while in a melted condition is likely. Additionally, the fact that Eschewy describes self-bonding webs of polycaprolactone homopolymer demonstrates that microphase separation, a feature of the current invention, is not present since the phenomenon of microphase separation between dissimilar segmental compositions is not possible within a homopolymer system.

It is this inherent limitation of homogenous semicrystalline polymer systems requiring interfiber bonding prior to solidification from the melt that the current invention intends to overcome. In such homopolymer systems, the ability of continuous filament web fibers to contact and self-cohere to themselves must be accomplished before solidification of the filaments from the melt. Since polymer solidification is a function of temperature, the external boundaries of the fibers are the first to cool and, as a consequence, the first to solidify. This rapid solidification of the fibers' outer boundaries functionally diminishes the possibility of creating inter-fiber attachments with later contacting fibers. It is the intention of the present invention to overcome this limitation of requiring interfiber contact prior to solidification and to functionally achieve the goal of delivering a self-cohering continuous filament web where interfiber attachments are formed after the polymeric components have solidified.

SUMMARY OF THE INVENTION

In view of the foregoing, it is seen there is a need for a web which:

provides for autogenous cohesion between the constituent fibers at physical points of contact;

by virtue of autogenous cohesion precludes any subsequent requirement for further mechanical entanglement, thermal processing, or the addition of polymeric or copolymeric adhesive binders or adjuncts to facilitate interfiber bonding to effect or achieve effective web cohesion;

provides for autogenous attachment between the produced web and other objects of a sufficiently similar substantially amorphous polymeric or copolymeric composition to provide crystallization and autogenous bonding between the objects at the physical points of contact; and provides for a bioresorbable web which, as a result of its single component or homogenous composition, can be used as an implantable medical device that delivers a more consistently homogenous bioresorption profile than would be expected of an implant with distinct structural features of different compositions.

In light of the aforementioned deficiencies:

It is an object of this invention to provide by utilizing melt spinning techniques and semi-crystalline polymeric materials a web which, by virtue of temporarily suspending crystallization of its component fibers at a substantially amorphous incomplete level of crystallization, provides for autogenous bonding between the constituent fibers at their physical points of contact.

It is a further object of this invention to provide such a web fabricated from semi-crystalline polymeric materials which, by virtue of its autogenous bonding capability provided through the inhibition of crystallization, precludes any subsequent requirement for further mechanical entanglement, thermal processing, or the addition of polymeric or copolymeric adhesive binders or adjuncts to facilitate inter-fiber bonding to effect or achieve effective web cohesion.

It is a further object of this invention to provide such a web which, by virtue of kinetically or thermodynamically temporarily suspending crystallization in a substantially amorphous incomplete level of crystallization, provides for autogenous bonding between the produced web and other objects of a sufficiently similar, substantially amorphous polymeric or copolymeric composition.

It is a further object of this invention to provide a web which preserves the amorphous homogenous disordered phase miscible condition achievable within the melt by sufficiently rapid cooling of the web's component fibers from the melt to a temperature below either the polymer's glass transition temperature or, in the case of temporarily miscible polymer systems, the temperature of its disorder-order transition to prevent polymeric crystallization.

It is a further object of this invention to provide a web that is a self-cohering, continuous filament, non-woven implantable medical device fabricated at least partially from semi-crystalline polymeric or block copolymeric materials which, by virtue of its autogenous bonding capability provided through the inhibition of crystallization, precludes any subsequent requirement for further mechanical entanglement or the addition of adhesive binders or adjuncts to effect or achieve effective web cohesion.

It is a further object of this invention to provide a self-cohering, continuous filament, non-woven implantable medical device fabricated utilizing melt spinning techniques from at least partially semi-crystalline block copolymeric materials of at least partially phase immiscible block compositions wherein the microphase separation potentiated by the initial block segment incompatibility provides an initial inhibition of the rate of crystallization, thereby extending the available time at a particular temperature that physical contact can occur between uncrystallized fibers or other objects prior to subsequent crystallization.

It is a further object of this invention to provide a self-cohering, continuous filament, non-woven implantable medical device fabricated utilizing melt spinning techniques from at least partially semi-crystalline block copolymeric materials of at least partially phase immiscible block compositions wherein the provision of the incompatible blocks in a solid homogeneously mixed condition potentiates, when placed in contact with other identically conditioned objects, an ensuing at least partial phase separation which provides for polymeric chain mixing between the contacting objects and a correlating reduction of the distinction between objects that results in an enhancement of inter-object adhesion.

It is a further object of this invention to provide a self-cohering, continuous filament, non-woven implantable medical device fabricated utilizing melt spinning techniques from at least partially semi-crystalline polymeric or block copolymeric materials of at least partially phase immiscible compositions under processing conditions which will deliver a homogenous disordered state of polymeric mixing sufficient in longevity to provide for to assembly of a cohesive web or other structure wherein the contact points between structures are established prior to subsequent at least partial phase ordering of the homogenous state and crystallization of the crystallizable polymeric or copolymeric segments.

It is a further object of this invention to provide a self-cohering, continuous filament, non-woven implantable medical device fabricated utilizing melt spinning techniques from at least partially semi-crystalline polymeric or block copolymeric materials of at least partially phase immiscible compositions wherein the amorphous homogenous disordered phase mixed condition possible within the melt is preserved through sufficiently rapid cooling to a temperature below the mixture's order-disorder transition to substantially prevent subsequent ordering or crystallization of the copolymer's semicrystalline segments.

These objects are met by a web of continuous filaments which are made of at least one semi-crystalline polymeric component covalently bonded as a linear block copolymer with or blended with one or more semi-crystalline or amorphous polymeric components. The filaments are intermingled together to form a porous web of filaments, the filaments having multiple contact points with each other within the web. The filaments are bonded at the contact points without requisite for added adhesive binders, adjuncts or post extrusion melt processing. The web may be bioresorbable. The web may be provided in forms with relatively high cohesive shear strength. The polymeric components of the filaments exist, at least temporarily, in a homogenous substantially phase miscible uncrystallized state. If preserved in the homogenous substantially phase miscible uncrystallized state, the object can then be manipulated into a distinct desirable molded shape and then subsequently set or crystallized to retain the desired form particularly suitable for a specific use or application.

DETAILED DESCRIPTION OF THE INVENTION

Definition of Terms

Figure 1:
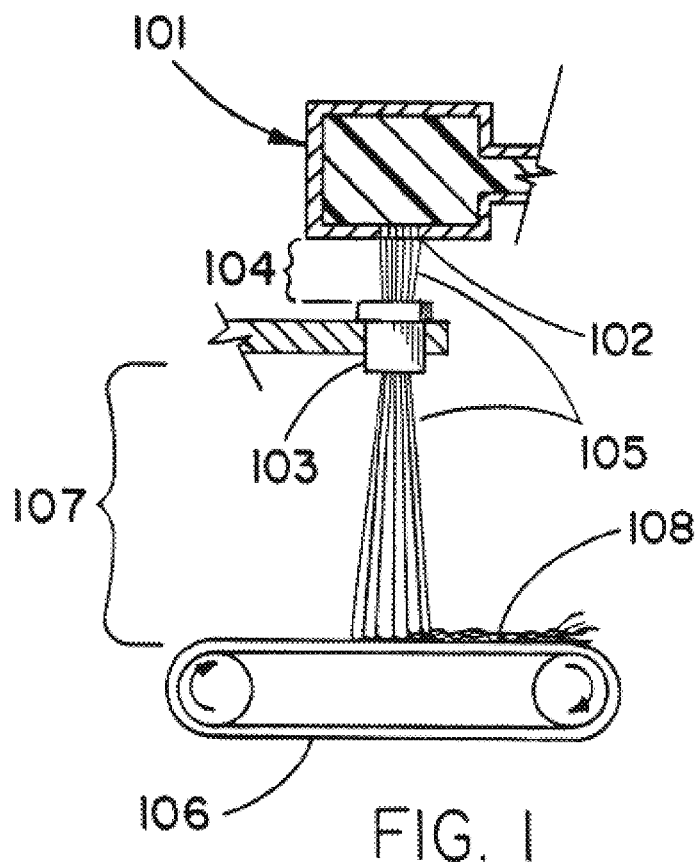
FIG. 1 depicts a schematic diagram of the layout of of the web producing extrusion system.

By "Fiber" is meant a cylindrical or tubular structure wherein the length is much larger than its diameter or breadth which is less than 500 microns (micrometers).

By "Continuous Filament" is meant a fiber or fibers of substantial length to unending length.

By "non-woven" is meant a type of fabric made directly from fibers or filaments or from a web of fibers without the preliminary yarn preparation needed for weaving or knitting.

By "sheet" is meant either a flexible or rigid layer which is very thin in its thickness relative to either its breath or width. For the purposes of this application, a sheet consists of deposited filaments and the thickness or smallest dimension of such a sheet shall not exceed 5 mm (0.2 inches).

By "web" is meant a sheet made by laying down or assembling fibers.

By "porous" is meant a material possessing a sufficiently open structure to allow for the passage of physiological fluids and/or living mammalian cells.

By "cohere" is meant the ability of filaments within a fibrous web to effectively stick or attach to themselves without the need for thermal or melt processing, or adhesive binders or adjuncts.

By "cohesive" is meant the ability of a material to hold itself together as a mass.

By "self-cohering", "self-bonding" or "autogenous-bonding" is meant the ability of a melt formed structure, or component thereof, to effectively self-generate an attachment to itself without the requirement to undergo a melt, or undergo the requisite addition of supplementary adhesives, binders, or adhesive adjuncts either before or after structure formation.

By "3-d web" is meant the laying down or assembling of fibers to form a structure thicker than a sheet (as previously defined).

By "shapeable" is meant the ability of a structure to conform or adapt to a particular contour, form, pattern, or fit.

By "quench" is meant the substantial inhibition of crystallization within a semi-crystalline polymer specimen by means of rapid thermal cooling to a temperature below the polymer system's glass transition ($T_g$) or order-disorder transition temperature ($T_{odt}$).

By "setable" is meant the retention of the ability to convert a crystallizable polymeric or copolymeric web or 3-d web from a thermodynamically unstable (metastable) condition possessing limited crystallinity to an alternative substantially thermodynamically stable level of crystallinity. This conversion cannot be effectively reversed short of the complete remelting and reformation of the web like structures. The conversion is facilitated by either the exposure of the web to solvents, lubricants, or plasticizing agents that facilitate chain mobility, the application of heat, or a combination thereof.

By "implantable" is meant a biocompatible device retaining potential for successful surgical placement within a mammal.

By "implantable device" is meant any object implanted through surgical, injection, or other suitable means whose primary function is achieved either through its physical presence or mechanical properties.

By "bioresorbable" is meant those materials of either synthetic or natural origin which, when placed into a living body, are degraded through either enzymatic, hydrolytic or other chemical reactions, into by-products which are either integrated into or expelled from the body. It is recognized that in the literature "resorbable", "absorbable", and "bioabsorbable" are frequently used interchangeably with this definition.

By "alternating copolymers" is meant copolymers with a regular or alternating repeating unit sequence whereby crystallization potential is substantially reduced due to segmental sequencing which prevents substantial crystallization from occurring.

By "thermoplastic elastomers" is meant a melt processable copolymer which possesses elastomeric mechanical properties as a result of a crystallizable "hard" segment and an amorphous "soft" segment possessing a $T_g$ below its service temperature.

By "blends" is meant polymeric materials that are melt mixed to achieve compounding between two or more different polymeric compositions that are not covalently bonded to each other. For the purposes of this application, a melt miscible blend is a polymeric mixture which possesses sufficient miscibility in the melt to provide for its extrusion into filaments.

By "additives" is meant substances added to polymers or polymeric systems that modify one or more of its properties.

By "semi-crystalline polymer" is meant polymers or copolymers which retain the eventual ability to crystallize upon solidification or annealing at temperatures above the $T_g$ in homopolymeric systems or above the highest component $T_g$ in multicomponent polymeric systems. Since uncrystallized segments of polymer chains exist in even the most highly crystalline of polymers, any polymer which crystallizes is generally considered as semi-crystalline.

By "phase miscible" is meant the homogenous mixing of dissimilar polymeric repeating sequences to produce either a stable or unstable condition possessing substantially no repeating sequence concentration gradient.

By "phase immiscible" is meant the segregation of dissimilar polymeric repeating sequences into macroscopic or microscopic regions that possess enhanced concentrations of similar or like polymeric repeating sequences. This term shall not be construed to refer to like polymeric sequences segregating into regions of crystalline and amorphous phases of the same polymeric sequence composition.

By "microphase immiscible" is meant phase immiscible regions of a dimension that is microscopic in scale and is not observable with the naked eye.

By "adhesive" or "binder" is meant a distinct component of the web that provides for bonding between the web's fibrous or filamentous components at their contact point interface. The bonding component can be administered and bonding effected through solution, heat, or other processes that substantially retain the properties of the web's structural supporting filaments.

By "adhesive adjunct" is meant a distinct separable additive which imparts adhesive or bonding qualities into an otherwise nonadhesive material. An example is the use of solvents, tackifier resins, or polymer softening agents blended with a melt processable polymer to produce a temporary or ongoing stickiness or tackiness which can result in an apparent self-cohesion. For the intent and purposes of this invention, tackifier resins are oligimeric materials with a weight averaged molecular weight of less than 5,000.

General Description of the Invention

This invention relates to self-cohering non-woven webs constructed from continuous filaments formed from semi-crystalline multicomponent polymeric systems which, upon the achievement of an equilibrium state, possess some evidence of phase immiscibility of the system's constituent polymeric components. The particular ability of the fibrous components of the webs of this invention to self-cohere to themselves or other similarly prepared objects is believed the result of a reduced rate of crystallization within the web's fibers when compared with rates typical of melt processed fibers. This crystallization rate depression is believed advantageous by preserving the melt's substantially homogenous amorphous non-crystalline phase mixed condition within the solidified quenched filamentous web until such a time that it can come into physical contact with other fibers or objects sustained in a similar amorphous condition of limited crystallization. The resulting interfilament or interfiber bonding that occurs in this invention can thus be accomplished without any requirement for adhesive binders or adjuncts, and additionally does not hold requirement for additional secondary mechanical entanglement, thermal, or compressive processing.

The autogenous self-cohesion that occurs between the filaments of the current invention is able to be produced from a semi-crystalline polymer blend or copolymer wherein the crystallization rate is sufficiently slowed to provide for sustained physical contact between solidified amorphous objects prior to substantial microphase separation and crystallization of at least the surface of the melt fabricated objects. More particularly, the observed crystallization rate depression is believed provided by the solidification of a homogenous melt miscible condition existing between two at least partially phase immiscible polymer systems. Physical contact between fibers or other objects existing in this relatively tacky solidified metastable homogenous state of phase miscibility provides the basis for an initial physical adhesion between the objects. Once such initial adhesive contact has been made, any ensuing phase separation of the initially miscible polymeric components offers potential for further enhancement of polymeric chain mixing across the joined objects' physical contact or bonding interface. More particularly, the invention utilizes a thermoplastic semicrystalline polymeric blend and/or block copolymer system processed in such a manner that from the melt a substantially amorphous solid condition is induced and maintained for a sufficiently extended period of time to provide for contact and combination with other similarly produced objects. The duration of the time period required for joining such temporarily amorphous substantially semi-crystalline objects remains dependent on the size of the produced object, the crystallization rate of the particular polymer system being utilized, the temperature of the melt, the temperature and volume of the cooling air or gas, and the eventual web retrieval and storage temperatures.

The invention also relates to a method for achieving a retarded crystallization rate and subsequent autogenous bonding of polymeric components by preferential selection and use of semi-crystalline polymeric blends and/or copolymeric materials. The prolonged amorphous state attainable by utilizing at least partially phase immiscible blends or block copolymers results from the preservation of the homogenous disordered fully miscible microphase unseparated state expected of polymeric materials when in a melted or flow processable condition. This condition is believed to be preserved through a sufficiently rapid rate of cooling that, due to elevated viscosity and reduced chain motion, substantially inhibits either full or partial microphase separation and consequentially sustains the substantially disordered state of the melt after both cooling and melt solidification. Suspension in such a disordered state of miscibility is believed to inhibit the subsequent crystallization that would be expected of a progressively more phase ordered structure, thus providing a continuation of an unstable malleable amorphous condition which allows shaping of the produced web into a virtually unlimited array of shapes which can then be retained after subsequent crystallization.

The self-cohering filaments of the current invention differ from the self-cohering fibers common to melt blown webs by the current invention's development of interfiber or interfilament bonding after their solidification from the melt. This post-solidification bonding feature provides for the continuous filament nature of fibers of the current invention and contrasts with the discontinuous characteristic of melt blown fibers that are deposited directly from a melted state. These differences are exemplified by both the consistent nature and larger fiber diameters (>10 $\mu$m) found in the current invention when compared with that of the smaller (<1 $\mu$m diameter) diameter fibers typical of melt blown webs. Additionally, the continuous filaments of non-woven webs of the current invention may possess relatively enhanced levels of molecular orientation when compared with melt blowns.

The current invention preferentially utilizes block copolymers that can be described as diblock, triblock, or multiblock which possess at least partially phase immiscible segmental components when in a thermodynamically stable state. Block copolymers are typically referred to as A-B for diblock, ABA for triblock, or combinations thereof for multiblock copolymers. Additionally, three or more components may be used to create a block copolymer, as in the case of an ABC terpolymer (also known as a tripolymer or ternary copolymer) exemplified by the bioresorbable PGA/TMC/PDS copolymer utilized in Biosyn® sutures that is available from U.S. Surgical Corporation, Norwalk, Conn., USA and contains one amorphous and two crystalline segments. A block copolymer which has within its composition a segment that is soft and rubbery at its service temperature would potentially possess elastomeric properties and could thus be described as a block copolymer thermoplastic elastomer (BC-TPE). Phase immiscibility in the context of block copolymers in intended to refer to segmental components which, if a part of a blend of the correlating homopolymers, would be expected to phase separate within the melt.

More particularly, the invention preferentially utilizes an ABA triblock copolymer system composed of poly (glycolide), also known as PGA, and poly(trimethylene carbonate), also known as TMC, to form a bioresorbable implantable non-woven web; wherein A comprises between 50 and 85 weight percent of the total weight, and wherein A is comprised of glycolide recurring units; and B comprises the remainder of the total weight and is comprised of trimethylene carbonate recurring units said material being bioresorbable and implantable. Details concerning synthesis of this copolymer can be found in U.S. Pat. No. 4,429.080 which is hereby incorporated by reference. A diblock construction of the same PGA:TMC segmental components is detailed within U.S. Pat. Nos. 4,243,775 and 4,300,565 which are hereby incorporated by reference. A 33% weight to weight ratio of TMC to PGA triblock copolymer may be obtained from Sherwood/Davis & Geck, Danbury, Connecticut.

Alternatively, other bioabsorbable components could be utilized in the polymerization dependent on the desired physical, mechanical, or bioabsorption rate properties needed for the intended implant application. However, polymerization must result in block segments of sufficient length to form at least one or more crystallizable components to the system. A system for use as an implantable which utilizes an amorphous segmental component would preferentially possess a segment $T_g$ which is higher than −50° C. and lower than 70° C.

Other semi-crystalline multicomponent polymer systems which possess phase miscibility within the melt but result in at least a partial phase separation upon equilibrium may be utilized to form a self-cohering web if conditions are maintained where contact between filaments and the related interfiber bonding can be effected prior to the phase separated equilibrium. Such self-cohering web forming conditions have been observed when utilizing the crystallizable poly-beta-hydroxybutyrate-hydroxyvalerate (PHB:PHV) copolymers. Additionally, self-cohering webs have also been achieved utilizing a blend of the bioresorbable poly(p-dioxanone) and PGA homopolymers. In both of these systems, evidence of at least a partial phase separation can be observed by the presence of multiple DSC endothermic melt peaks.

It is believed that the temporary suspension of a phase immiscible polymer system within a homogenous amorphous phase miscible metastable condition which affords assembly of a self-cohering continuous filament web can be achieved with other crystallizable block copolymer systems. Such polymer systems are believed to include segments selected from the group consisting of polyesters such as poly(butylene terephthalate) and poly(ethylene terephthalate); poly(vinyl alcohol); poly(vinyl acetate) and partially hydrolyzed forms thereof; hydrogel type polymers such as poly(hydroxyethyl methacrylate), poly (hydroxypropyl methacrylate), and the like; polysulphones such as poly(phenylene-sulphone); polyurethanes; segmented polyurethanes; polyether urethanes, polyesterurethanes, polycarbonate urethanes, poly(urethane ureas) polyamides; poly(ethylenes); poly(propylenes); and poly(carbonates). If a bioresorbable constructions are desired, such polymer systems are believed to include polymer segments selected from the group consisting of poly (glycolide); poly(carbonates); poly(dioxanone); poly (lactides); poly(d-lactide), poly(l-lactide), poly(d,l-lactide), poly(lactide-co-caprolactone), poly(caprolactone), poly (hydroxybutyrates), poly(hydroxyvalerates); and poly (hydroxybutyrates-co-valerates).

Polymeric & Processing Requirements
Phase Miscibility and Microphase Separation

The ability of any two or more component polymeric systems to achieve a state of phase miscibility, be it based on block copolymers, blends, and/or other polymer systems, remains dependent on a variety of factors that influence the interactions between neighboring polymeric chains. Discussions of factors such as the Flory-Huggins solubility parameter, especially as it relates to miscibilities of bioabsorbable polyester blends systems, can be found in the following references:

G. Rocha and S. McCarthy. Polymers in Biodegradable Surgical Devices: Blending (Poly(glycolic acid) with other Biodegradable Plastics. *Medical Plastics and Biomaterials*, May/June 1996, 44–48.

Y. Cha and C. G. Pitt. The biodegradability of polyester blends. *Biomaterials*, 11 (March 1990),108–112.

Regardless of the driving mechanism, the existence of full phase miscibility in such a multi-polymeric component system may be observed through the presence of a $T_g$ which substantially follows the Fox equation. In this equation, which is usually applied to compatible random or alternating copolymers, the observed glass transition temperature is a composition dependent function averaging the constituent components of the homogenous mix. The specific Fox relationship is:

$$\frac{1}{T_g} = \frac{W1}{T_{g1}} + \frac{W2}{T_{g2}} + \cdots$$

wherein W represents the respective mass fractions of the copolymeric component and the respective temperatures $T_{g1}$ and $T_{g2}$ reflect the glass transitions (expressed in degrees Kelvin) of the respective components in homopolymeric form. In the case of a temporary miscibility in blends or block copolymers reflective of a disordered or homogeneously mixed substantially single phase condition, the temperature of the order-disorder transition (ODT) above which a quenched mixture of specific components begins to segregate into a more ordered or separated phase condition is sometimes referred to as the order-disorder transition temperature ($T_{odt}$), or the microphase separation transition temperature ($T_{mst}$). This temperature, like that of random or alternating copolymer systems, is also composition dependent, and can also be affected by the partial miscibilities of polymeric components. An excellent discussion of the thermodynamics surrounding this transition temperature can be found in the article entitled: Block Copolymer Thermodynamics: Theory and Experiment, Annu. Rev. Phys. Chem. 1990, 41, 525–57 by F. S. Bates and G. H. Fredrickson.

In the context of the current invention, a condition of either permanent or temporary phase miscibility is identifiable through the existence of a single $T_g$ or $T_{odt}$ which substantially follows the predictions of the Fox Equation. The presence of the single $T_g$ or $T_{odt}$ has been observed in various multiple component polymer systems as is discussed within the following references:

P. Xing, et al. Miscibility and Crystallization of Poly(β-hydroxybutyrate) and Poly(p-vinylphenol) Blends. *Macromolecules*, 30 (1997), 2726–2733.

M. C. Luyten, et al. Morphology in binary blends of poly(vinyl methyl ether) and E-caprolactone-trimethylene carbonate diblock copolymer. *Polymer* 3(1997), 38, 509–519.

G. O. Shonaike. Studies on miscibility of glass fibre reinforced blends of polyethylene terephthalate with polybutylene terephthalate. (needs reference revision; *European Polymer Journal*, 28 (1992), 777–781.

Besides the preceding articles, the following provide additional references discussing variations in the nature and temperature of the $T_g$ of miscible and partially miscible systems:

J. N. Clark et al. Reexamination of poly(methyl methacrylate)/poly(epichlorohydrin) blends by small angle neutron scattering and differential scanning calorimetry. *Polymer*, 33(1992), 3137–3145.

M. Song, et al. Modulated differential scanning calorimetry: 4. Miscibility and glass transition behaviour in poly(methylmethacrylate) and poly(epichlorohydrin) blends. *Polymer*, 37(1996), 25, 5561–5565.

Any achieved phase miscibility can, dependent on the polymeric system, exist in a condition that either remains stable or, alternatively, exist in a metastable miscible-like state of transition toward a condition of increasing immiscibility as polymeric chain movement and reorganization potential is allowed. Some evidence about the nature and stability of these molecular interactions between chains may be elicited by comparing the thermal characteristics expected of fully miscible systems with that of actual DSC thermal analytic data performed on polymeric systems suspected of being less than fully miscible. In such thermal comparisons, blend and copolymeric systems that exist in a state of full component miscibility within their amorphous phase, be it in a metastable or equilibrium state, are expected to display a single $T_g$ or $T_{odt}$ occurring at a temperature that is a function of the systems composition and substantially predictable when utilizing the Fox equation. Conversely, fully immiscible multiphase amorphous systems are expected to display distinct $T_g$'s which correlate with the homopolymer analogs for each separated immiscible phase.

Between the aforementioned scenarios of full homogenous phase miscibility and complete phase separation there exists a condition of partial polymeric phase miscibility. If a condition of partial miscibility is present, the DSC scan can be expected to reveal a $T_g$ occurring at a temperature between that of the correlating homopolymer analog and one of full component miscibility as predicted by the Fox equation. In such partially miscible systems, this shift of $T_g$ toward the homopolymer's $T_g$ delivers evidence of an enrichment of the system's amorphous phase with polymeric constituents similar to that of the homopolymer. In any system, such phase enrichment with a particular polymeric constituent would strongly imply a correlating reduction of that same constituent within other regions. In completely amorphous phase separating systems, this constituent enrichment would have to result in its correlating depletion within other regions of the polymer system's amorphous domain. However, in semi-crystalline polymer systems such constituent enrichments can lead to crystallization resulting in the subsequent removal of the crystallizable component from the amorphous domain. This removal of constituents by crystallization results in a continuing further enrichment of the amorphous phase with the non-crystallizing component and the consequential progression of the experimental $T_g$ toward that of the non-crystallizing component's homopolymer analog.

When complete crystallization is achieved in a semicrystalline system, then the non-crystallized balance of the polymeric system must, of necessity, be present within the system's non-crystallizing amorphous phase. If the amorphous phase is composed exclusively of non-crystallizing monomeric components, the resulting $T_g$ would be analogous to that of the correlating non-crystallizing homopolymer. Conversely, components within the crystallized regions can no longer be detected by the presence of a $T_g$, a characteristic attributable exclusively to amorphous regions possessing greater chain mobility. If, however, some crystallizable or other constituents remained miscible within the existing amorphous phase due to reasons such as steric constraints or segment inclusions, the resulting $T_g$ would be affected by their presence. As a result, the $T_g$ of such a partially phase miscible system would be shifted away from that of its non-crystallizing homopolymer analog toward a temperature reflective of the constituent ratio existing within the amorphous phase, a value which could be interpreted utilizing the Fox equation.

Although the formation of polymeric crystals is not generally recognized to occur between dissimilar constituents, inclusions of other polymeric constituents may be encountered within the lattice produced by crystallizing polymeric segments. Such non-crystallizing or amorphous inclusions, when present in sufficient concentrations, can be expected to produce a diluent or colligative effect resulting in a depression of the melting temperature from that expected of a crystallized homopolymer analog. This observed evidence of melting point depression can also be attributed to crystalline imperfections and reduction of lamellar thickness. Alternatively, immiscible semi-crystalline polymer systems which, upon reaching thermodynamic equilibrium phase separate into regions of relatively greater purity resulting in the formation of less diluted crystals, would therefore produce a correlating higher DSC melt point. Also, if inhomogeneity within the sample exists that either affects the amount of inclusions present within a crystalline sample or produces variations in the level of sample phase separation, multiple DSC melt peaks may be encountered reflecting the differing diluent effect on the formed crystals.

Determination of the Order-disorder Transition (by DSC)

Phase immiscibility in either an exclusively amorphous or semicrystalline web system can be evidenced by any substantial deviation of the polymer system's $T_g$ from that predicted by the Fox equation for the sample's established ratio of polymeric components. For a system with multiple amorphous components, the existence of correlating additional $T_g$'s would provide evidence of additional separated amorphous phases of the differing polymeric compositions. Conversely, for semicrystalline systems possessing an amorphous component, deviation from the amorphous $T_g$ predicted by the Fox equation correlated with the presence of a DSC crystalline melting peak provides evidence of effective separation and crystallization of a particular polymeric component from the miscible amorphous phase condition. In such a semi-crystalline system, a partially miscible system would result in the depression of the observed Tm while a fully phase separated system would retain a $T_m$ similar to that of the homopolymer analog.

Since block copolymers are composed of differing homopolymer segments connected together through covalent bonds, regions with characteristics of the respective homopolymer are created when similar segments are attracted to each other causing phase immiscibility. In an ordered, two component, block copolymer system where both segments can crystallize, this resulting microphase separation would result in two melting points representative of the two crystallizable segments. The glass transition for such polymers may be obscured and even eliminated by the crystallization which has tightened the tie chains sufficiently to eliminate molecular motion sufficient to produce a $T_g$. Alternatively, if the two component system was composed of phase immiscible amorphous segments, then two different $T_g$'s would be expected for each of the resulting ordered amorphous block copolymer segments. The current invention that utilizes PGA:TMC possesses both a crystallizable and an amorphous segment that results in a $T_g$ for the amorphous block and a melt peak for the crystalline block.

As described earlier, an ordered block copolymer system possesses distinct segments that produce $T_g$'s representative of their homopolymer analogs. Conversely, the same block copolymer in a disordered state possesses characteristics which are a composite of the two mixed polymeric constituents. If one induces a quenched disordered homogenous condition through sufficiently rapid cooling either by extrusion processing or through cooling capabilities of a DSC, the temperature above which reorganization of this mixture into segregated segments becomes possible is considered the temperature of the order-disorder transition ($T_{odt}$). Since the properties of the homogenous disordered condition are dependent on the composition ratios between the two polymeric constituents, the temperature of this occurrence can be predicted by utilizing the Fox or the Gordon-Taylor-Wood equations that are commonly applied to polymer blends, and sometimes applied to random copolymers.

Preferred Embodiment

The particular ability of the amorphous components of this invention to self-cohere when utilizing the earlier described polymer selection criteria and processing conditions can be utilized to produce a continuous filament non-woven web that provides for autogenous interfilament bonding of the web's fibers without any mandatory requirement for the use of adhesive binders or adjuncts or for secondary thermal processing to obtain a cohesive non-woven web. The web produced when utilizing the specifications of the current invention yields the continuous 20 to 50 micron diameter filaments which are common to spunbond non-wovens. However, the current invention does not require the subsequent bonding processes typical of spunbond processes.

One embodiment of the current invention provides for a self-cohering web comprised of an at least partial phase separable melt miscible blend of at least two homopolymers where at least one of which is semi-crystalline and the rate of polymeric crystallization may be controlled kinetically or thermodynamically.

Another embodiment of the current invention provides for a self-cohering web comprised of an at least partial phase separable and controlled crystallizable blend of a homopolymer and block copolymer, where at least one of which is semi-crystalline.

Another embodiment of the current invention is a self-bonding or self-cohering web comprised of an at least partial phase separable and controlled crystallizable semi-crystalline block copolymer system.

The preferred embodiment of the current invention is a self-bonding or self-cohering porous non-woven comprised of an ABA block copolymer of a preponderance of repeating sequential units of glycolide possessing the formula:

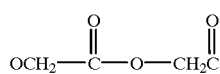

A and repeating sequential units of trimethylene carbonate possessing the formula:

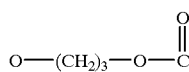

B

The end groups in this block copolymer are well known and can be —OH, —COOH, or derivatives thereof. The amount of A in the ABA block copolymer can range from 50% to 85% by weight. The inherent viscosity at 30° C. in hexafluoroisopropanol (HFIP), can range from an average of 0.5 dl/g to over 1.5 dl/g, and preferably, for preferred use as a barrier used in bone regrowth can range from 0.8 dl/g to 1.2 dl/g. The acceptable melting point for this particular range of copolymer compositions as determined through a DSC melt peak can range from approximately 170 to 220° C.

The PGA:TMC copolymerization is achieved by a sequential addition ring opening polymerization of the cyclic trimethylene carbonate and glycolide dimer monomers. The synthesized block copolymer can either be acquired directly from Davis & Geck (Danbury, Conn., USA) or prepared through the synthesis methods detailed within U.S. Pat. Nos. 4,243,775 and 4,429,080 described earlier. Both monomers are available from BI Chemicals, Petersburg, Va., USA. Other desired polymeric compositions and structures may necessitate the use of different polymerization conditions and/or methods.

The web is first produced from the block copolymer by a procedure similar to spunbonding. The procedure is first to dry the granulated or pelletized block copolymer to free it of any volatile components or residual moisture. Then the copolymer is melted in an extruder equipped with a multi-orifice fiber spin-pack or spinneret to allow formation of continuous filaments. The continuous filaments are then accelerated within a Transvector connected preferentially to room temperature air and directed in a generally vertically downward direction. The Transvector air stream, which may be varied in temperature to either accelerate or slow the rate of phase separation and crystallization, acts to attenuate or draw the emerging fibers and to control the rate of fiber flow. The produced fibers of the preferred embodiment are entrained in room temperature air to produce fibers that typically possess molecular orientation and are between 20 and 50 micron in diameter.

The produced fibers are then deposited by puddling in a mass of continuous randomly disposed filaments that physically contact and appear to adhere and become physically linked at crossover points to form a porous cohesive web without the need for adhesive binders or adjuncts or for additional thermal bonding processes. The filaments as spun appear visually solid and appear not to stick to most objects within which contact is made, but do adhere readily to each other at said crossover points. Unlike usual spun-bonded fibers, the fibers of the copolymers used herein are self-cohering as they collect on a surface positioned underneath the spinneret. In other words, the spinning conditions are adjusted to provide a tackiness to the emerging fibers which allows them to self-cohere as they collect in a cohesive random pile, or web, on the collecting surface. In other words, the fibers as they strike the collecting surface are solid fibers, but still tacky enough to bond to each other. In contrast, the PGA homopolymer extruded in a similar fashion is not tacky and does not form a coherent or cohesive web.

To produce the preferred embodiment, the fibers are randomly deposited on a movable belt upon which they make contact at crossover points to produce the self-cohering web. By moving the collecting surface along a planar path, the web formed will be in the shape of a sheet, the density and pore size of which can be directly affected by the collector's linear velocity. Consequently, at high collector velocities, macroporous webs with very low area and volume densities, and thicknesses hypothetically reducible to that of the fiber crossover height are possible. Conversely, low velocities produce more fiber deposition over a given area thereby reducing pore size and producing higher volume density for a given fiber diameter. By allowing the spinneret to remain in a fixed position, the deposited sheet will be thicker along its center while tapering to the sides due to the fact the spinneret has more orifices in the center and less along its sides. By moving the spinneret from side to side, a substantially flat sheet can be obtained. If the collecting surface is not moved, what can be described as a 3-dimensional fibrous block capable of an indeterminate thickness can be built up with the resulting web porosity and density at least partially a function of the applied air velocity, the resulting fiber diameter, and the accumulated height (i.e. compressive weight) of the web.

Initially, after retrieval of the now cohesive web from its room temperature cooling and collection conditions, the web is resilient and can be shaped at temperatures that are above its "quenched" $T_{odt}$, between −5 and 30° C. dependent on the specific PGA:TMC copolymer ratio. Accordingly, this substantially amorphous uncrystallized web, prior to any subsequent microphase ordering, can be shaped into any configuration the web can be manipulated into, one of which could be to fit and cover a defect under which bone regrowth can take place. During such in vivo use the copolymer is gradually bioresorbed through the combination of hydrolysis and enzymatic activity that progressively reduces its molecular weight and eventually returns the constituent polymeric segments into their original repeating units which are then dispelled or assimilated in vivo. Thus, the longevity of the web in vivo is at least partially dependent upon the size of the block copolymeric segments and the molecular weight of the copolymer.

This concept is useful for other applications where structural support is indicated or separation of specific cell varieties is desirable. Examples of such applications are surgical meshes intended for soft issue repair, nerve repair and nerve guidance applications, adhesion prevention, and bone and hard tissue regeneration.

Extrusion Conditions

In the case of block copolymers under extrusion conditions, a minimal level of mixing is believed to result in disordering of the polymer chains so that when exiting the spinneret as fibers the blocks of a melted copolymeric system are believed to be in a substantially homogenous disordered condition. The copolymer's cumulative thermal exposure over time needs to be minimized sufficiently to prevent transesterification reactions that can result in degradation of the copolymer's block and correlating phase immiscibility characteristics. When cooled from the melt, it is known that the polymeric chains of most block copolymers at equilibrium possess phase-immiscible segments that undergo rearrangement from the homogenous disordered condition of the melt through a self-assembly process into an ordered and microphase separated condition, a condition highly characteristic of BC-TPEs. This rearrangement of the constituent polymer chains into a more ordered condition is provided by the chain mobility present in the rubbery state existing between the melt temperature and that of the order-disorder transition temperature ($T_{odt}$), the temperature above which this transition from disorder to order can proceed. If crystallizable segments are present within the now ordered microphase separated regions, a crystallization process analogous to that of a similar homopolymer system can subsequently proceed.

In the current invention, as the spun fibers exit from the spinneret die, the still molten filaments are entrained into an accelerated air current provided by a Transvector which both accelerates the fibers, thereby potentiating molecular orientation, while imparting a drop in the fibers' temperature from that of the melt. It is the temperature of this entrained air and that of the ambient conditions wherein the spun fibers are collected that dictate the ability, or lack thereof, to impart an amorphous self-cohering condition into the produced fibers.

The $T_{odt}$ of the multicomponent polymeric system must be at a sufficiently high temperature that spontaneous micro-ordering and crystallization does not occur before inter-object adhesion can be achieved. The rate of such micro-ordering and crystallization is affected significantly by the thermal conditions in which the web is retrieved. In the case of PGA:TMC where the $T_{odt}$, dependent on copolymer ratio, is between 0° C. and 25° C., chain mobility is sufficiently slowed to effectively inhibit microphase ordering while the web is being retrieved at room temperature. Conversely, a crystallizable polyester ether thermoplastic elastomer with a $T_{odt}$ of −25° C. would be expected to provide higher chain mobility at the same room temperature web retrieval conditions and consequently would be expected to more rapidly micro-order and subsequently crystallize before interfiber bonding could occur.

Additionally, in order to attain interfiber bonding under similar room temperature conditions, the $T_{odt}$ must be sufficiently low that the room temperature cooled fibers remain reasonably above the $T_{odt}$ where spontaneous interfiber adhesion will occur upon contact. If the thermal environment into which the web is retrieved is substantially below the $T_{odt}$ where the amorphous disordered mixture enters a glassy condition, chain mobility is expected to become sufficiently reduced to prevent interfiber attachment from occurring upon filament contact.

Filament Cohesion

Crystallization from the homogeneously mixed condition expected when cooling directly from the melt is believed to occur only if sufficient microphase reorganization is realized to allow agglomeration of the crystallizable segments. This physical requirement for movement of the chains to achieve the thermodynamically stable microphase separation condition is believed to occur not only within the fiber structure, but also across fibers in the regions where physical contact and surface adhesion has occurred. After such inter-object contact has been achieved to the extent that the amorphous, homogenous, disordered interfaces have combined, further maintenance at temperatures above the $T_{odt}$ will allow for continuing crystallization or microphase separation ordering. The ordering process is believed to extend between adequately joined but previously separate objects to provide a bridge leading to a mixing effect between the two joined surfaces that provides, upon microphase separation, for an enhanced intermingling of the constituent polymeric chains. Such ordering and subsequent crystallization results in the potential for both the elastomeric soft segment and the crystalline hard segment regions to bridge the region where the two objects were joined. It is this microphase reorganization that is believed to effectively create a phase integration between the two fibers or objects that is essentially of the same chemical and physical composition as the fibers and consequently delivers the enhanced inter-filament bonding strength observed in the produced web.

The resulting surface integration created by this microphase mixing is not believed to follow the normal definition of adhesion since bonding is effected solely with the substrate material and consequently no identifiable compositional interface exists between the two intersecting surfaces. The result is a bond believed to possess strength approaching that of the constituent block copolymer, generally stronger than what would be expected of less integrated adhesives covering the same amount of intersecting area. The produced bond is also believed to be potentially superior to adhesion produced through normal polymeric crystallization since chain mixing would be more integrated with the current invention than that of a single phase system that crystallizes with minimal molecular movement. However, this particular interfiber bonding may be reduced as molecular orientation increases and the benefits may be offset by the increased fiber strength inherent to such increased orientation.

Such microphase separations or micro-orderings can vary in size due to copolymeric composition ratios and can arrange themselves to various shapes. A variety of shapes between phase components ranging from spherical inclusions to laminar alternating arrangements either parallel or perpendicular to the former surfaces of melt produced but now joined objects are possible. Such varieties of ordering shapes across the contact surfaces of the two joined objects provides a mechanism for bonding which differs from that of normal surface to surface adhesion delivering an integration of ordered phases which, if formed perpendicular to the joined surface, potentially imparts almost covalent bond strength levels of attachment between the former surfaces of similarly prepared objects.

Since the adhesive mechanism driving attachment is dependent on another similarly prepared object, the produced material in its disordered amorphous state preferentially bonds to itself with little observed affinity to other objects. This provides processing benefits by minimizing risk of the fibers attaching or sticking to objects such as the Transvector, collector screen, or processing object. This is specifically the case with the preferred embodiment PGA:TMC web which possesses a distinct affinity to itself rather than to other objects.

In bonding of similarly conditioned homogeneously disordered structures, actual assembly of the components occurs under thermal conditions below the melting point of the polymer system and above the order-disorder transition of the amorphous quenched system. This component assembly can occur directly by inducing collisions or other interfiber contacts as they are cooled from the melt and before temperatures below the $T_{odt}$ are realized. Optionally, if cooled with sufficient rapidity to a temperature below the $T_{odt}$, exposure of the produced material to the chain mobility of the rubbery state existing above the $T_{odt}$ can be minimized or eliminated to a point where microphase separation and crystallization can effectively be averted. If successful, the fibers or other melt formed product can through this rapid quench approach be induced into retaining the homogenous disordered condition by continued maintenance at temperatures below the $T_{odt}$ where a glassy state is maintained and chain mobility and chain intermingling is minimized. Under these thermal conditions, microphase separation ordering does not occur until temperatures are sufficiently raised and chain mobility is reintroduced. Any subsequent temperature increase above the $T_{odt}$ delivers the accompanying chain mobility that reinstitutes interaction between similar block copolymer surfaces and continuing rearrangement toward the most stable ordered configuration again possible.

Generally described, the blend or block copolymeric systems of the current invention are able to autogenously bond to other structures of similar amorphous condition after solidification from melt. To attain this end, the amorphous objects produced from the melt must achieve physical contact within the temperature range below that of the semi-crystalline material's melt temperature and above that of the single glass transition temperature representative of the thermodynamically unstable homogenous phase miscible condition, also known as the order-disorder-transition temperature in block copolymer systems. Exposure of the homogenous object to temperatures within this range can provide for self-tackiness and self-cohesion in amorphous quenched objects if completed prior to substantial achievement of phase equilibrium. Conversely, temperatures within this range additionally and competitively promote both ordering and phase separation in both semi-crystalline polymeric blends and block copolymers leading to both a loss of tackiness and the ability of fibers to adhere to themselves and other objects of similar conditioning. As a result, for any particular blend or copolymer system a limited time duration exists wherein the amorphous condition attachment can occur before sufficient levels of crystallization effectively prohibit self-cohesion to occur.

Bonding between amorphous components is achieved through their physical contact after solidification from the melt and before substantial crystallization has occurred. The duration of the time prior to substantial crystallization wherein bonding can occur can range from seconds to years dependent on the crystallization rate of the polymer selected, the size of the produced object, and the post processing temperatures the produced object is exposed to.

Alternatively, chain mobility and the ensuing microphase separation and crystallization may be enhanced through the use of plasticizing agents that effectively lubricate or facilitate chain movement within the solidified polymer. Such agents can be plasticizers or other similarly acting additives that can be introduced into the polymer system at any point before, during, or after introduction into the melt. Such polymer plasticization can additionally be accomplished by the application of volatile solvents, such as acetone or chloroform, which penetrate the solidified polymer's interstices to provide a temporary lubrication of the polymer chains that facilitates molecular movement and a transition to the more stable crystallized or ordered state.

Features of the Produced Web

In general, the non-woven webs produced utilizing the current invention possess opposing surfaces and are porous through and between the opposing surfaces, a feature which delivers a recognizable value in a variety of applications. However, the construction of the non-woven web of the current invention delivers particular physical features and benefits which are either difficult or impossible to achieve, either individually or combined, when utilizing other non-woven web fabrication technologies. These benefits are considered to be by virtue of this invention's objective of effectively retarding the rate of crystallization producing the resulting amorphous condition within the deposited fibers.

As described previously, the current invention provides integral non-woven webs possessing interfiber self-cohesion from a single melt composition without requirement for the addition of adhesives, binders, solvents or other adjuncts. Additionally, this feature eliminates any processing requisite for mechanically induced interlocking, or the application of calendaring or other forms of compression based deformation (with or without heat) to achieve interfiber attachment. It also eliminates the secondary thermal compression processing required to soften coated fibers, sheath/core fibers, or the lower melting fiber inclusions that provide for interfiber bonding in multicomponent heat fusible webs. Beside possessing a melting or softening point lower than that of primary fibrous structure being bonded, these components are typically materials with different physical and mechanical properties that, in turn affect the final properties of the web.

Reduced Web Density

As a consequence of self-cohesion, webs of the current invention possess a reduced apparent web density or overall weight from that which would be expected of an identical web construction produced from the same material but not processed in a manner that effects autogenous inter-fiber bonding. Additionally, since any adhesive or binder necessitated in the absence of autogenous bonding would inherently displace additional space within the external boundaries of the produced web, the result of autogenous bonding would be a relatively less dense and more open structure than if added binders were required. This feature is a disadvantage if a maximum amount of web loft for tissue ingrowth is desirable.

Consistent Degradation Characteristics

Since the overall stability of any structure fabricated from any single component is generally simpler to predict than a similar structure fabricated from multiple compositions, the autogenously bonded single component webs of the invention are expected to possess a more predictable morphological stability over a variety of conditions than would the same composition when combined with additional components. Additionally, if designed for degradation either in a landfill or after implantation in a mammal, a single component web would be reasonably expected to deliver a more predictable overall degradation pattern than would a similar web with additional components. In the case of bioabsorbable materials, a more consistent decomposition or bioresorption rate is believed to lead to a more consistent and predictable implant integrity in vivo. Consequently, this single composition provides the benefit of a homogenous bioabsorption which both minimizes the loosening of fibers due to either the inherent differences in modulus between multiple materials and due to inconsistent bioabsorption rates inherent to the combination of two materials.

Molecular Orientation within Fibers

Despite the fact that the web of the invention produces a level of spontaneously developed interfiber bonding not expected outside of a melted condition, the produced self-cohered fibers have been observed to retain molecular orientation within the produced filaments. Other self-bonding or self-cohering continuous filament webs have been reported in U.S. Pat. No. 4,163,819 and U.S. Pat. No. 5,575,874 for non medical implantable applications, but neither delivered specific reference to the ability to retain molecular orientation after development of the self-cohering non-woven structure. Although inducement of molecular orientation is dependent on a variety of conditions during extrusion processing, the capability to deliver relatively consistent molecular orientation within a web which can spontaneously develop inter-fiber self-cohesion without the requisite for adhesive binders, adjuncts, or thermal compression methods is believed unique.

Fiber Alignment/Web Integration

Usual spunbond webs are constructed of continuous filaments that are relatively straight and free of notable curvature within the axis of the fibers. This is believed to be the result of the spunbond drawing process and the related solidification and cooling of the fibers prior to their deposition onto the collector mat. Since the solidified spunbond fibers possess minimal free suppleness and curvature when deposited onto the collector, they tend to layer upon themselves, bridging across prior fiber depositions with broad gaps orders of magnitude larger than the component in-between the fiber's diameter. This stratified deposition pattern generally produces a visually observable open porosity.

The material of the current invention as a result of fiber cooling and crystallization after deposition, is believed able to achieve higher web densities than would be expected of usual spunbond processes produced from straighter and more rigid fibers at the time of deposition on the collector mat. With the present invention, the fibers as deposited in an amorphous condition are more ductile than their more crystalline counterpart and, as a result, deposit in a more variable fashion producing more crimps or waves within any particular fiber thereby resulting in a more dense deposition than would be expected of more rigid fibers. This increased curvature of the fibers consequently delivers greater levels of intermingling and entanglement among component fibers than would be expected from the limited interaction with non-proximal layers and broader spans found in conventional spunbond's deposition of stiffer and more straight fibers. Consequently, the current invention is believed to deliver a web with an increased level of fiber entanglements when compared with the levels inherent to traditional spunbond processes.

The practical result of this combination of increased entanglement and integration of fibers with autogenous bonding at fiber contact points is both a reduction in the web's potential for fraying and an improvement in its cohesive strength when measured by shear forces applied to the plane of web deposition. This result is a function of the combination of integral self-cohesion of the individual fibers at contact points and the general entanglement of the web with other fibers deposited more deeply within the cross section of the membrane. These characteristics contrast with prevailing spunbond constructions where an attempt to remove fibers from the stratified layers of a spunbond web's surface is relatively easier since it does not involve as many entanglements with other fibers deposited within the interstices of the web. As a result, resistance to surface fiber removal in conventional spun bond processes involves only the rupture of the fiber-fiber bonds which connect that surface-exposed fiber to the fibers immediately below it. Conversely, if the fiber at the surface was not straight but possessed undulations or ripples, as in the current invention, these features would increase the chance of interfiber entanglements and consequently the net energy required to remove a fiber from the surface of the web. In the current invention, this web cohesion through fiber entanglement is further augmented by the interfiber bonding that is imparted without the use of adhesive binders or adjuncts, or thermal compression processes.

Fiber Alignment/Web Smoothness

Webs produced in accordance with the current invention deliver a smoother web when compared to other spunbond materials since the continuous fibers or filaments are more likely and frequently integrated into the interstices of the web. This more integrated fibrous material with relatively reduced void presence within the topmost surface layer consequently delivers a smoother surface texture that is less apt to experience fraying or fiber separation from the surface than would a normal spunbond counterpart.

The continuous filament nature of both this and normal spunbond webs eliminate the frequency of fiber ends with a reduction in the presence of fibrous protrusions above the external dimensions or boundaries of the produced web. This absence or reduction in the frequency of fiber terminations provides improved smoothness to the web, especially when compared with staple fiber based webs and felts which possess significantly larger amounts of fiber terminations and, as a consequence, a rougher texture to the web surface.

Improved General Web Strength

The improved cohesive strength afforded by combined autogenous bonding and filament entanglement properties of the described web can be best observed when compared with other single composition fibrous webs, such as felts, that are dependent solely on mechanical integration and entanglement for web cohesion, yet possess no direct interfiber bonding. However, upon evaluation of a variety of other spunbond constructions, including some which utilize adhesives binders, it was unexpectedly found in an example contained herein that the web of the current invention almost doubled the cohesive strength value of the highest strength webs as measured under lap shear. Additional appreciation can also be obtained through noting the relative ease with which fibers can be separated from poorly cohesive, thermally compressed webs where autogenous fiber bonding is a result of heat and compression on already solidified and crystallized polymeric materials. Additionally, the web of the current invention, by virtue of its fibrous construction, provides significantly higher web cohesive strength when compared to other non-fiber based porous non-woven structures such as sponges and other similar non-film based non-fibrous porous structures known to those skilled in the art. In addition, the frequency and strength of the interfiber bonding of the current invention delivers a three-dimensionally integrated structure which is believed to provide for a cohesive web possessing enhanced flexural strength when compared to other self-cohering non-woven web forms with the same fiber diameter, volume density, and composition.

Combination of Web with Other Materials

The benefits that are derived from the cohesive strength and consistent biodegradation profile offered by the described self-cohering non-woven web construction may be later optionally combined with desirable additives, coatings, or other components added to either the stabilized or unstabilized web. Such treatments may be beneficial for a variety of reasons, such as the modification of adhesive or surface properties, the reduction of as-fabricated porosity, or the delivery of drugs or other desirable chemical, biological, or bioactive agents. By virtue of the web's single component construction, addition of such additives is not subject to considerations inherent to the multiple substrate compositions, such as susceptibility of the binder to solubility or degradation considerations when exposed to a carrier solvent for the additive.

As with virtually any sufficiently porous construction, various bioactive agents and carrier materials can be introduced or loaded into the porous interfiber interstices of the web. Bioactive agents in this context refers to osteoconductive substances, osteoinductive substances, growth factors, chemotactic factors, morphogens, pharmaceuticals or drugs, catalysts, proteins, peptides or other biologically active molecules or genetically altered or native state living cells of autogenic, allogenic, xenogenic, or recombinant origin that induce an intended biological response. Such substances include, but are not limited to, transforming growth factor beta (TGF-beta), bone morphogenetic proteins (BMP's), osteogenic proteins, antibiotics, organic or inorganic antimicrobial agents, vascular endothelial growth factor (VEGF), basic fibroblast growth factor (bFGF), platelet derived growth factor (PDGF), insulin-like growth factor (IGF), insulin and immunoglobulin type G antibodies. Such an application could be the introduction of a bioactive antimicrobial agent, such as the silver agents described within U.S. Pat. No. 5,019,096, into the porous structure of a fibrous web with the intended biological response of inhibiting microbial colonization within the implant.

Introduction of a bioactive agent into the interfiber interstices of the web can, in some applications, be achieved simply by solvating or suspending the agent within a carrier solvent that readily penetrates the porous interstices and is then evaporated or extracted to deposit the bioactive agent within the porous substrate. However, in many applications such simple deposition techniques can result in overly rapid diffusion rates from the porous structure. The elevated diffusion rate of simple deposition can be mitigated by including a controlled release polymeric component that is codeposited with the bioactive agent and provides an immobilizing structure which inhibits salvation, dissolution, or diffusion of the bioactive agent into the surrounding physiological fluids. Additionally, cells that are either genetically altered or in a native state can be seeded into web for delivery of bioactive agents.

Such codepositions of bioactive agent and controlled release substrate can be achieved simply in the form of solid inclusions such as powders, nanospheres, microspheres, or microcapsules that are mixtures of the polymer and the bioactive agent that can be retained within the porous structure through mechanical means. The bioactive agent can be suspended within the substrate in the form of an included particle, or it can be molecularly dispersed within the polymer to effectively act as a soluble, intimately-mixed plasticizing agent. Either approach effectively reduces the bioactive agent's diffusion rate into the adjacent or ingrown tissue due to the presence of the codeposited polymer. In addition to diffusion, bioresorbable polymers can in themselves regulate release of bioactive agents as a result of their own degradation process Alternatively, codeposition may be achieved by the application of an adhesive coating where a layer of polymer that controls release of the bioactive agent is adsorbed onto the fibrous structure where it is effectively immobilized, and from which diffusion of the bioactive agent occurs. Such an applied coating layer can alternatively be of a chemical formulation possessing chemically reactive groups that can provide for covalent interlocking or cross-linking of the polymeric molecules in situ, subsequently immobilizing the coating around the fibers. Alternatively, linkage can be designed to occur between the immobilizing polymer and the bioactive agent, thereby creating a chemical mechanism with which to control bioactive agent release. Consequently, composition of the selected bond will determine the rate of its scission in vivo and consequently the release or desorption rate of the bioactive agent into the surrounding tissue.

Simply providing for penetration of bioactive agents into the amorphous interstices of controlled release polymeric structures is commonly known to those skilled in the art. However, the extended metastable condition that exists after the extrusion of webs produced with the current invention provides a unique quality for facilitating penetration into or attachment of soluble bioactive agents to the web fibers under conditions that are much less severe than that possible with melt or conventional solvent dissolution techniques. The ability of the metastable amorphous web to absorb relatively biocompatible solvents such as acetone and water which then facilitate subsequent crystallization offers the unique ability to introduce bioactive agent solutes into the polymer interstices along with the solvent where they can be immobilized within the crystallizing structure. Penetration would be dependent on the bioactive agent's molecular size and solubility within the polymer. Complete dissolution or entrapment within the crystallizing polymer would be possible with species of relatively low molecular weight, such as steroids. Alternatively, entrapment of pendant side chains of polymer-insoluble, larger bioactive molecules such as proteins could provide for their immobilization adjacent to the polymer surface where a continuing but physically immobilized bioactivity could occur. The final polymer properties would then become a function of the concentration of the bioactive agent additive and its cumulative effect on polymer chain interactions.

The relatively reduced temperatures at which the web's filaments self-cohere additionally provides an opportunity for the unique ability to add and evenly distribute solid inclusions within the interstices of the web as it is being formed. Additionally unique is the ability to readily add solids that are larger than the pores of the web, that possess melting or deformation temperatures which would result in potentially severe deformation under higher temperature filament deposition or bonding conditions, or that would dissolve in the solvents utilized in dry-spinning, solvent-based web formation processes. Such solid inclusions could be in the form of microspheres, or of coated or uncoated particles containing one or more bioactive agents. Such an approach overcomes common concerns for uneven distribution of particles when introduced into fully formed webs, especially those where the intended application dictates a limited or restricted pore size.

The article of the present invention may therefore incorporate any of the above defined bioactive agents in a coating on an exterior surface of the web, a coating on the interior surfaces of the void spaces of the web, within or as solid inclusions within the web, or as a component of the filament material.

Unlimited (3-d) Web Thickness

Due to self-cohesion and fiber integration characteristics combined with the elimination of any requirement for compression processing requirements, the webs of the invention are believed to provide superior web thickness capabilities than can currently be attained when utilizing either conventional melt blown or spunbonding non-woven processes. The fact that the web self-coheres as it is being formed provides instant interfiber bonding upon which additional, equivalently-bonded fiber layers may be applied to produce an instantly cohesive web without any requirement for the application of adhesives or binders, or heated compression processes. Consequently, with polymer systems which readily quench into an amorphous homogenous phase, only apparatus based dimensional limitations prevent the recognition of an unlimited thickness web continually building and bonding onto the underlying layers.

Such capacity provides for the simple production of densely packed three dimensional porous fibrous web based structures that would be difficult to produce utilizing compression based non-woven methods.

Shapeable Webs

The preservation of the ductile and formable amorphous non-crystalline and homogenous disordered state expected after the web formation and prior to any phase separation and crystallization may be achieved through rapid cooling of the formed web to a temperature below the $T_{odt}$ or miscible system $T_g$. If the melt and web are cooled with sufficient rapidity, the reduced temperatures will limit chain mobility and consequentially arrest any further progress in either the ordering and phase separation of a block copolymer system and, if comprised of semi-crystalline polymer components, any subsequent crystallization of those components. Such ordering of the block copolymeric phases would be expected to be especially limited in polymer systems in the glassy state below the homopolymer constituents' glass transition temperature. Such depressed thermal conditions can be expected to maintain such an amorphous homogenous state indefinitely until temperatures are raised and chain mobility is sufficiently increased to provide for chain reorganization and crystallization.

If such conditions are maintained and minimal, to no crystallization is present, the produced ductile, formable, and shapeable, substantially amorphous web can be subsequently shaped at temperatures above its $T_{odt}$ into virtually any desirable form into which it can be manipulated. This can be undertaken at various times and locations ranging from manufacturing processes which immediately follow web formation to the ultimate consumer provided that precautions preventing microphase separation and crystallization for the utilized polymer system are undertaken.

Additionally, bonding of similarly quenched and preserved substantially amorphous objects may again be achieved by raising the temperature of the objects to be joined above the homogenous single but separable phased system's order-disorder-transition temperature. Once above the $T_{odt}$, sufficient physical contact to produce intersurface mixing between like amorphous objects of similar condition can result in autogenous bonding between those objects. Such inter-object bonding may be in addition to the interfiber bonding already achieved within the webs.

Once the desired form of the shapeable article has been achieved, methods other than direct heat can be utilized to induce microphase separation and subsequent crystallization of the web. Such microordering of the structure can alternatively be achieved by enhancing chain mobility through the use of plasticizing agents that facilitate chain movement within the solidified amorphous polymer. Such agents can be included with the polymer at any point before, during, or after introduction into the melt. Such plasticization or polymeric lubrication can additionally be accomplished by the application of a sufficiently permeating volatile solvent, such as acetone, which penetrates the solidified polymer's interstices to provide a temporary lubrication of the polymer chains that then facilitates molecular movement and a transition to the more stable crystallized or ordered state. Chain movement can also be facilitated by the presence of moisture, which can also be combined with heat as is the case when a web is exposed in vivo to blood or in vitro to saline solutions maintained at 37° C.

Medical Applications of Self-Cohering Webs

The variety of forms which can be derived from the webs of this invention, if fabricated from known biocompatible polymeric components under appropriate controls known to those skilled in the art, may be utilized for implantable applications such as in membranes utilized for guiding the regeneration of tissue lost to periodontal disease. Although some of the aforementioned structural and physical benefits of a continuous filament self-cohering non-woven web component can be recognized if utilized in an implantable device fabricated from a non-bioresorbable polymer system, the benefits of a self-cohering web produced from a single melt composition is of particular benefit in bioabsorbable implantable polymer systems due to the expected consistency of its mechanical property degradation throughout the bioabsorption process.

In the case of bioresorbable materials, additional benefit is gained with the elimination of added binders or adhesives intended to impart cohesive strength to the web, but necessitates an additional material's eventual biological resolution, and thus bioresponse, upon degradation. The reduction of an implantable device to a single structural composition provides the engineering benefit of delivering a single bioabsorption profile; rather than the alternative of having to coordinate in vivo loss of mechanical properties in structural features that possess differing compositions and, consequently, differing bioabsorption patterns.

Consequently, there remains a need for a bioresorbable membrane material for use in mammalian applications that delivers sufficient porosity to provide for ingrowth and attachment of tissue, possesses sufficient cell barrier properties to maintain separation of tissue types, and maintains sufficient rigidity to provide the needed space to allow bone regeneration within the treated defect. Of particular need is the membrane to deliver sufficient conformability to mold to the contours of the bone surrounding the defect. Consequently, it is especially beneficial if the material is shapeable or moldable upon demand into shapes specific to the bone contours surrounding the treated defect and then becomes rigid once in place to ensure preservation of the desired space proximal to the defect. Moldability is desirable in order to shape the material into desired contours of the regenerated bone. Rigidity is desirable in order to maintain the space in which bone growth is desired.

The porous webs of the invention, as formed, are shapeable into a variety of shapes either during manufacture or anytime prior to microphase separation and crystallization. This constitutes one aspect of the invention. In another aspect of the invention, the invention is directed to a rigid or microphase separated solvent set or heat-set material. The invention also relates to the utilization of such webs in implantable medical devices in various dimensional forms for a variety of applications. The material referred to covers a bone defect in a mammal to protect said defect from ingrowth of tissue, other than bone tissue. The material can be shaved or trimmed, then "set" or, first "set" and then cut, shaved, or trimmed to a distinct desirable shape.

Additionally, the self-cohering web of the current invention can be utilized as a component within a multicomponent construction, such as a construction similar to that of Resolut® Renerative Material as described within PCT #WO92/10218. In that construction, a cell occlusive layer of one component exists between two porous fibrous layers of another component to provide for tissue ingrowth and attachment without allowing cells to penetrate through the plane of the membrane. The self-cohering web of the current invention can be utilized to provide the porous tissue integrating component which can then be laminated to either side of a cell occlusive layer provided by another component.

Still other related aspects of the invention include processes for making the materials described above and processes for using said materials.

EXAMPLES

Example 1

Preparation of Web

67% poly(glycolide) 33% poly(trimethylenecarbonate) (w/w) triblock copolymer was acquired from Davis & Geck (Danbury, Conn.)—Lot #10-CV-9433. This bioresorbable copolymer is commonly referred to by Davis & Geck as polyglyconate.

Approximately 25 mg of the acquired copolymer was dissolved in 25 ml of hexafluoroisopropanol (HFIP). The produced dilute solution was found to possess an inherent viscosity (IV) of 1.53 dl/g when measured using a Cannon-Ubelodde viscometer immersed in a 30° C. (+/−0.05° C.) water bath.

Approximately 10 mg of the acquired copolymer was placed into an aluminum DSC sample pan, covered, and analyzed utilizing a Perkin-Elmer DSC 7 equipped with an Intracooler II cooling unit able to provide sample cooling to temperatures as low as −40° C. After preconditioning of the sample at 180° C. for 2 minutes, the sample was cooled at the maximum rate provided by the instrument (−500° C./min setting) and scanned from −40° C. to 250° C. at a scanning rate of 10° C./min. After completion of this initial scan, the sample was immediately cooled at the maximum rate provided by the instrument (−500° C./min setting). A second similar scan was undertaken on the same sample over the same temperature range. After scan completion and thermal maintenance at 250° C. for 5 minutes, the sample was again cooled at the maximum rate provided by the instrument and a third scan undertaken.

Each scan was analyzed for the observed $T_g$, $T_{odt}$, crystallization exotherm, and melt endotherm. The results are summarized in the following table.

|  | $T_g/T_{odt}$ | $T_g/T_{odt}$ Capacity | Exotherm Peak | Exotherm Enthalpy | Melt Peak | Melt Enthalpy |
| --- | --- | --- | --- | --- | --- | --- |
| Heat 1 | 0.2°C. | 0.26 J/g*° C. | none | none | 213.7° C. | 44.7 J/g |
| Heat 2 | 17.0°C. | 0.59 J/g*° C. | 113.7° C. | −34.2 J/g | 211.4° C. | 41.2 J/g |
| Heat 3 | 17.0°C. | 0.51 J/g*° C. | 121.4° C. | −35.3 J/g | 204.2° C. | 38.5 J/g |

Approximately 100 grams of the as delivered pelletized copolymer was heated overnight under vacuum at 130° C. Upon completion, the vacuum dried polymer was then allowed to feed into a half inch Randcastle screw extruder with an attached J. J. Jenkins fiber spinpack. Ultimately heated to a die or "spin pack" temperature of 225° C., the molten copolymer then exited the system through the bottom of a 7 orifice spinnerette (see "Spin Pack" in FIG. 1) consisting of 0.381 mm (0.015 inches) diameter die openings arranged in an approximately 2.16 cm (0.85 inches) diameter circular configuration.

An adjustable arm holding a Vortec Model 902 Transvector® (Vortec Corporation—Cincinnati, Ohio USA) was positioned below the base of the spinnerette (see FIG. 1) with the top of the Transvector inlet centered below the die openings at a distance ("A" in FIG. 1) of approximately 3.8 cm (1.5 inches). The Transvector was connected to a room temperature (20–25° C.) pressurized air source regulated at approximately 30 psi. When operating, the pressurized air introduced and accelerated within the Transvector's throat draws additional air into the inlet from the area of the multiple orifice die.

The polymer was allowed to feed into the screw extruder and through the crosshead of the spinneret, eventually exiting as a melt through the die in the form of 7 individual filaments. As the filaments became influenced by the air current entering the Transvector inlet, the filaments were accelerated through the Transvector at a significantly higher velocity than without the provided air entrainment. The accelerated filaments were then accumulated on a screen fabric collector belt (see FIG. 1) located at a distance ("B" in FIG. 1) 66 cm (26 inches) from the die surface and moving at the speed of approximately 23 cm/min (0.75 feet per minute). The resulting fibrous web that accumulated on the collector belt possessed a relatively consistent loft along the direction of belt movement, while the amount of accumulated filaments diminished in height on either side of the centerline when observing in line with the direction of belt movement.

After greater than 10 seconds of cooling at ambient temperature, the web was removed from the fabric belt and examined. The retrieved article was found to be a tactilely supple, cohesive fibrous web where individual component fibers did not appear to fray or separate from the web when subjected to moderate handling. The filaments were intermingled and bonded at contact points.

Example 2
Characterization of Example 1 Web
Filament Diameter

Figure 2:
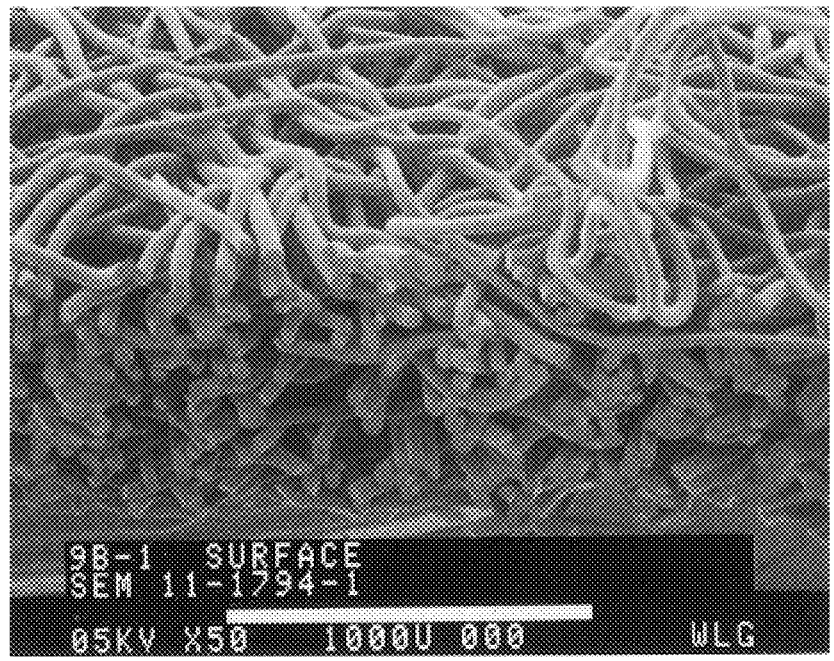
FIG. 2 depicts angled 50× magnification scanning electron micrograph (SEM) of representative web surface and cross-section.

A sample of the cohesive web produced in Example 1 was observed utilizing both light microscopy and scanning electron microscopy (SEM) at magnifications between 20× and 1000× (see FIG. 2 for example). The examined web was found to be composed of fibers ranging in diameter from approximately 20 to 100 micrometers.

Web Bonding Characteristics

Further examination of the contact points between fibers utilizing both light microscopy and SEM at 1000× showed the web's fibers to physically intersect with each other with limited distortion or deformation of the contacting fibers' cylindrical form or nature. This observed physical intersection and interfiber contact was assumed to be autogenous self-cohesion since no adhesive binders or adjuncts had been added to the copolymer either before, during, or after the extrusion process described in Example 1.

No Noticeable Fraying

Visual examination also revealed minimal fraying or protrusion of individual fibers outside the planar boundaries of the produced web. This condition remained after thermal conditioning at 75° C. and moderate handling of the web.

Inherent Viscosity

Approximately 29 mg of the produced cohesive web was dissolved in 25 ml of hexafluoroisopropanol (HFIP). The produced dilute solution was found to possess an inherent viscosity (IV) of 0.97 dl/g when measured using a Canon-Ubbelohde viscometer immersed in a 30° C. (+/−0.05° C.) water bath. Consequently, the IV was observed to have dropped during processing from the initial value of 1.53 dl/g in the pelletized copolymer to a value of 0.97 dl/g in the produced web.

Thermal Properties

Figure 3:
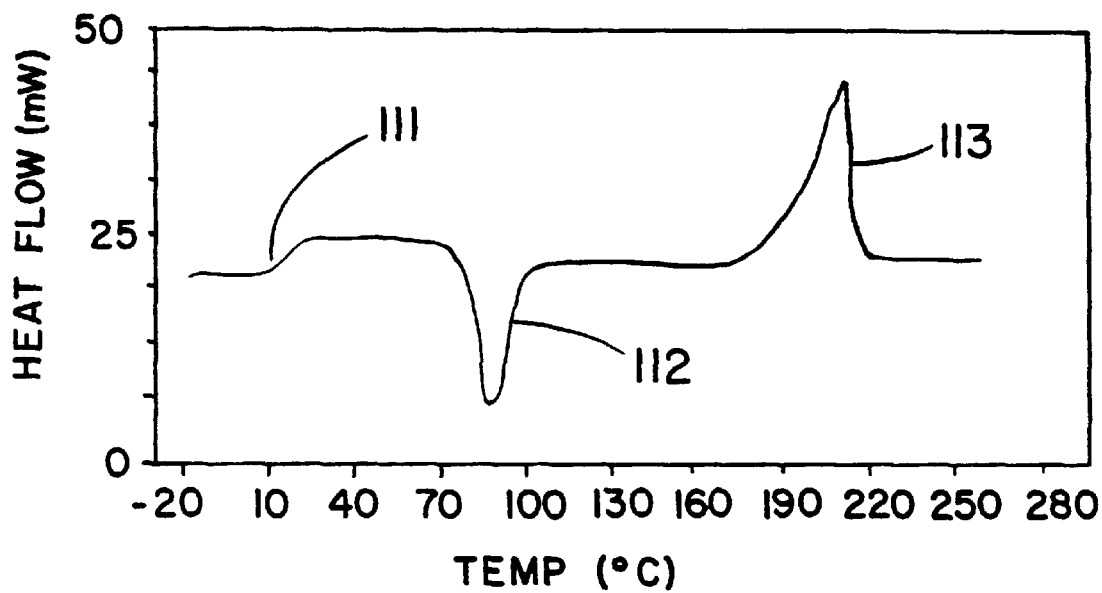
FIG. 3 depicts the characteristics of a typical differential scanning calorimeter (DSC) scan of a produced web in homogenous disordered condition.

An appropriately sized sample was obtained from the web produced in Example 1 to allow for its thermal analysis utilizing a Perkin Elmer DSC7 Differential Scanning Calorimeter. Scanning was conducted at 10° C./minute and the instrument's temperature was moderated with an Intracooler II refrigeration unit. A single scan between −20° C. and 250° C. was performed with the obtained results as follows:

The reported $T_{odt}$ occurs at the inflection point between the differing levels of heat capacity marked by a deflection of greater than 0.1 joule per gram-degree Celsius (J/g*° C.) in the baseline of the scan. This $T_{odt}$ occurs at a temperature between the $T_g$'s of the respective homopolymers and is roughly approximated by the Fox equation. In this particular example the web sample displayed an order-disorder transition at approximately 16° C. and a crystallization exotherm beginning at approximately 70° C. Full specimen crystallinity is considered proportional to the area under the melt endotherm, quantified by enthalpy in joules/gram(J/g). The general characteristics of a thermal scan of this web can be observed in FIG. 3.

Tensile Strength

Figure 4:
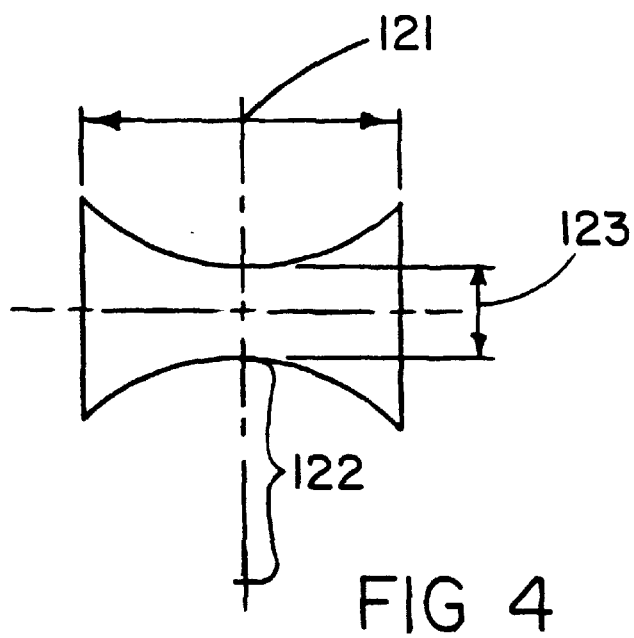
FIG. 4 depicts the dimensions of the tensile testing specimens utilized to evaluate the produced webs (see Example 2).

After conditioning of an appropriate sized section of web produced in Example 1 at 75°C. for 30 minutes with the intention of assuring the specimen's microphase separation and crystallization, a portion of the conditioned web was then cut into the test dimension depicted in FIG. 4. The as cut test specimen possesses a length of 0.150 inches (13.2 mm) that is trimmed at a radius of 0.375 inches (9.5 mm) from points centered 0.45 inches (11.4 mm) to either side of the specimen longitudinal centerline. This results in a specimen of width 0.150 inches (3.81 mm) that is then measured for its respective thickness and then placed into the tensile test apparatus with a grip separation distance of 5.0 mm. The gauge length in this specimen is considered to be the same as the grip distance of 5.0 mm. When the specimen was tensile tested at a constant crosshead speed of 50 mm/min, the thermally conditioned web was found to possess at maximum load tensile stress of 0.5 kg/ mm² (4.9 MPa) when tested after pre-conditioning in buffered saline at 37° C. for 1 hour. The Young's modulus for the same samples was found to be 1.17 kg/ mm²(11.5 MPa) and ranged from 0.5 kg/mm² (4.9 MPa) to 1.6 kg/mm² (15.7 MPa).

Gurley Stiffness

The web produced in Example 1 was retained for approximately 9 months under refrigerated conditions of approximately 3 to 5° C. At that time the web was removed from refrigeration and a series of 2.54×1.27 cm (1.0×0.5 inch) samples were cut. The stiffness of these unconditioned samples previously stored under refrigeration was then determined utilizing the Gurley Stiffness Test described within INDA standard test method #IST 90.2–86 utilizing a Gurley Stiffness Tester available from Gurley Precision Instruments, Inc., Troy, N.Y., USA. After completion of testing, the same samples were then conditioned for 1 hour by immersion in phosphate buffered saline at 37° C. The values for both the Gurley Stiffness and the Adjusted Gurley Stiffness (Gurley Stiffness divided by the weight of the sample web) are presented for both conditioned and unconditioned samples in the following table.

|  | $T_g/T_{odt}$ | $T_g/T_{odt}$ Capacity | Exotherm Peak | Exotherm Enthalpy | Melt Peak | Melt Enthalpy |
|---|---|---|---|---|---|---|
| Heat 1 | 16.32° C. | .54 J/g*° C. | 88.16° C. | −31.68 J/g | 209.70° C. | 45.49 J/g |

| Sample ID | Gurley Stiffness (unconditioned) | Gurley Stiffness (conditioned) | Adjusted Stiffness (unconditioned) | Adjusted Stiffness (conditioned) |
|---|---|---|---|---|
| SE18-DG-1 | 19.3 mg | 123 mg | 0.18 mg/mg | 1.17 mg/mg |
| SE18-DG-2 | 79.0 mg | 322 mg | 0.92 mg/mg | 3.74 mg/mg |
| SE18-DG-3 | 3.95 mg | 66.7 mg | 0.05 mg/mg | 0.91 mg/mg |

For each sample, conditioning at 37° C. resulted in an increase in stiffness at least 4 times that of the unconditioned web. This demonstrates the change in web stiffness that occurs in the transition between the disordered amorphous and solid ordered crystalline states.

Density

Three 1.27 cm (0.5 inch) diameter samples of the web were acquired and both their apparent or overall thickness and weight were determined. The resulting volume density of the three samples was found to be 0.28, 0.27 and 0.32 g/cm$^3$ while the area density of the same three samples was found to be 26.1, 29.3, and 28.8 g/cm$^2$ respectively.

Long Term Retention of Disordered State

After approximately two years of refrigerated storage (temperature maintained between 0–5° C.), the web sample was retrieved and approximately 10 mg of the web was placed into an aluminum DSC sample pan, covered, and analyzed utilizing a Perkin-Elmer DSC 7 equipped with an Intracooler II cooling unit able to provide sample cooling to temperatures as low as −40° C. After placement the sample was immediately scanned from—40° C. to 250° C. at a scanning rate of 10° C./min. The obtained results are summarized in the following table.

| | $T_g/T_{odt}$ | $T_g/T_{odt}$ Capacity | Exotherm Peak | Exotherm Enthalpy | Melt Peak | Melt Enthalpy |
|---|---|---|---|---|---|---|
| Heat 1 | 13.2° C. | 0.57 J/g*° C. | 76.2° C. | −28.4 J/g | 212.4° C. | 54.6 J/g |

The reported $T_{odt}$ of 13° C. shows its deviation from the $T_g$ values of 37 to 39° C. expected of PGA homopolymer and the −15° C. $T_g$ expected of the TMC homopolymer and consequently provides evidence that a state of at least partial phase miscibility had been achieved and retained within this particular sample.

Example 3

Shaping (Molding) of Web in 37° C. Water

Arch Form

After over 24 months continuous storage under refrigerated conditions, a 2.5 cm×2.5 cm section was obtained from the web described in Example 1 and characterized in Example 2. The section of web was formed into an arch and restrained so that the outside edges of the arch were separated by approximately a 0.7 cm distance. This distance is intended to approximate the width of a mandibular ridge. The web section was then immersed into a 37° C. water bath while maintaining its restrained arched configuration. After 10 minutes of 37° C. immersion, the piece was removed from both the bath and its restraint and allowed to return to room temperature. The web was found to have retained its arched configuration upon removal.

The preformed arched web was then restrained so that the separation between the outer opposite edges was approximately 2.0 cm apart. The restrained web was then reimmersed into the 37° C. water bath. Upon retrieval after 10 minutes of immersion and removal of the restraint, the web was found to have returned to the width of the original arch where the outside opposite edges were separated by approximately 0.7 cm distance.

The preformed arched web was then conformed into a flattened planar orientation and subsequently restrained in that position for approximately 30 seconds. It was found that the web returned to its original arched configuration.

Tube Form

An approximately 2.5 cm×2.5 cm section was obtained from the same web as described in Example 1 after over 24 months continues storage under refrigerated conditions. The section was wrapped around a 0.7 cm diameter mandrel so that one end of the membrane loosely overlapped the tube by approximately 0.25 cm. Sufficient pressure was then applied within the region of the overlap to create a visually observable self-attachment between the two overlapping edges of the web.

The now tubular web structure and mandrel was then immersed into the 37° C. water bath for 10 minutes. After removal, the web was removed from the mandrel and observed to retain its tubular shape. The now solidified, loosely overlapped region was cut from the tube. The produced tubular structure was found to be resistant to collapse when mild to moderate finger pressure was applied. If, however, sufficient finger pressure was applied to develop a collapse of the tube, release of that pressure resulted in substantial return to the original tubular configuration.

Thermal Analysis

Thermal characteristics of the overlapped region of this 37° C. conditioned membrane was evaluated in a manner similar to that described in Example 2. It was found that no observable $T_{odt}$ could be noted at 16° C., nor was a perceivable exotherm identifiable near 70° C. A TMC $T_g$ at approximately −15° C. could be noted in the scan. Numeric results are summarized in the following table and show the sample to be fully crystallized:

| | Todt | Todt Capacity | Exotherm Peak | Exotherm Enthalpy | Melt Peak | Melt Enthalpy |
|---|---|---|---|---|---|---|
| Heat 1 | not detected | not detected | not detected | not detected | 213.9° C. | 53.5 J/g |

Example 4

Synthesis and Extrusion of PGA:TMC Triblock a) A PGA:TMC triblock copolymer was synthesized. All synthesis works including pre-cleaning, post-cleaning, starting material unpacking, repackage, and the polymer package were carried out within a Class 10,000 clean room. All material contact equipment including surrounding components were thoroughly cleaned with isopropanol utilizing a particle free wiping sponge. All cleanings were done two hours prior to the reaction to allow for full drying.

A one liter reaction kettle was equipped with a high torque, speed controllable mechanical stirrer, temperature controlled heating system (thermo-couple was placed inside of the reaction kettle) and a dry nitrogen inlet and outlet. Anhydrous nitrogen was supplied into the reaction kettle in minimum flow rate during the course of the experiment. The reaction kettle was preheated to 165° C. under nitrogen. In a beaker, trimethylene carbonate (BI Chemicals, as received, 150.0 g), glycolide (BI Chemicals, as received, 6.00 g) were charged with diethylene glycol (Aldrich, as received, 0.051 ml). The mixture was warmed up to melt and then transferred into the kettle. SnCl2.2H$_2$O (Aldrich Chemicals, Milwaukee, Wis., USA—as received, 0.017 g) was also added into the kettle. The melted mixture was stirred at 185° C. under nitrogen with a moderate stirring speed. Polymerization took place in 20 minutes shown by observing an increase in viscosity. The viscous polymer was stirred under the same conditions for another 40 minutes. Glycolide (BI Chemicals, as received, 344.0 g) was added and the temperature was now set at 230° C. The polymerization was observed to occur in 20 minutes. The melted polymer was then stirred at 230° C. under nitrogen for another 40 minutes. The polymer was discharged. It solidified when it was cooled down to room temperature. Light brown polymer was obtained, grounded to small pellets and packaged into a pyrogen free plastic bag.

b) Triblock web Extrusion—The extrusion system used for this experiment was a ram, or pot system manufactured in-house. This type of system is typically employed in the fiber spinning industry for experimentation and analysis using relatively small amounts of polymer. The most widely used, commercially available example of this type of extruder is manufactured by Alex James & Associates, Greenville, S.C. The James extruder differs from the one manufactured in house primarily in the drive mechanism. The in-house system utilizes a hydraulic drive while the James system is gear driven using a DC drive. Both systems differ from typical synthetic fiber spinning equipment primarily by the method of polymer feed. In a ram system the polymer is pre-melted to a given temperature and forced through an orifice by use of a plunger. By nature, there is little temperature control or mixing and the process is not continuous. In a screw extrusion system the polymer is fed into the screw and compressed and mixed over the length of the screw. Temperature is generated primarily through drag friction along the barrel and controlled through the use of a barrel heating and cooling system. This is a continuous process system.

The hydraulic driven ram extruder used in producing this extrusion has a one inch diameter barrel and plunger. A seven filament spinneret was used with an individual filament diameter of 0.381 mm (0.015 inches). Heat is controlled at the barrel and spinneret. A Transvector with outlet dimensions of 32 mm diameter and a length of 1 cm was used to blow the fibers onto an endless collector belt.

The PGA:TMC synthesized in Part A was granulated and then vacuum dried for 15 hours at 1320 centigrade. 39 grams of polymer was placed in the extruder with the barrel and spinneret preheated to 225° centigrade. Polymer was allowed to melt for a period of 30 minutes prior to start of the extrusion process. The Transvector was placed directly below the die face at a distance of 1.91 cm (0.75 inches) from the face to the top of the Transvector inlet. Compressed air was supplied to the air inlet of the Transvector at a pressure of 0.24 MPa (35 psig). Hydraulic pressure of 1.38 MPa (200 psi) was applied to the ram to force the polymer through the spinneret and the collector belt was turned on. This caused the fibers attenuated by the force of the Transvector air velocity to randomly form a continuous web of approximately 5.08 cm (2 inches) in width. The individual fibers formed cohesive bonds at contact points producing a self-cohering web. The mean fiber diameter for five samples was measured at 29.2 microns.

Example 5

Characterization of Triblock of Example 4b

The web produced in Example 4b was then evaluated with the following results:

Tensile Testing

Tensile testing was conducted on the acquired web in a manner similar to that described in Example 2 above. The observed tensile stress of the produced web was found to range from 0.27 to 0.62 kg/mm$^2$ (2.6 to 6.1 MPa).

Example 6

Shapeable Placement in Canine

A canine subject previously scheduled for euthanization was administered the appropriate amount of anesthesia followed by the removal of all teeth in the left mandibular quadrant. The gingival flap was then laid using a surgical midline incision technique. A saddle type mandibular defect measuring 4.5 mm coronal to apical and 11.5 mm mesial to distal was then prepared. Utilizing five pieces of an amorphous quenched 2×2 cm PGA:TMC web from Example 4 maintained under constant refrigeration and weighing between 110 mg and 140 mg, an acquired web specimen was then trimmed utilizing surgical scissors to a size that provided coverage that extended approximately 3–5 mm past the edges of the created defect. The web's trimmings were retained for later thermal analysis utilizing DSC. A microwaveable plastic container holding approximately 1 liter of sterile water was then heated in a microwave oven to a temperature of approximately 60° C. The trimmed piece was then visually formed into an arched configuration that approximated the bony contours of the defect area to be treated. While restrained in the arched configuration with tweezers, the conformed web and pipette were then immersed into the now 58.5° C. water for 2.5 minutes. Upon removal it was noted that the web retained the conformed shape that was maintained during the immersion. The material was then placed over the created defect and found to substantially conform to the defect's bony contours.

An additional 2×2 cm piece was then acquired, trimmed, and formed over a finger into an arched configuration utilizing latex gloved hands. Utilizing acetone in a dropper bottle, drops of acetone were then applied to the formed web until it became completely wetted as determined visually with the applied solvent. After approximately 10 seconds of solvent exposure, the formed and now solidified web was immersed into warm sterile water (estimated temperature of 50° C.) for approximately 1 minute. Upon removal from the aqueous immersion, it was noted that the web substantially retained its shape at the time of application of the acetone drops. The material was then placed over the created defect and found to substantially conform to the defect's bony contours.

An additional 2×2 cm piece was then acquired, trimmed, and placed directly over the defect. While maintaining an arched configuration suitable for the defect contours, hot water was applied directly to the arched area of the placed web utilizing a 30 cc plastic syringe possessing a 30 gauge hypodermic needle and containing water at approximately 55° C. Upon completion of this in situ saturation of the web, it was noted that the web substantially retained its shape at the time that heated water was applied and was found to substantially conform to the defect's bony contours.

An additional 2×2 cm piece was then acquired, trimmed and restrained in an arched configuration utilizing latex gloved hands, Sufficient hot water was then applied with a needleless 30 cc plastic syringe to visually wet the crest area of the arched web. Upon cooling it was observed that the web retained its arched configuration and, when placed over the defect area, was found to substantially conform to the defect's bony contours.

An additional 2×2 cm piece was then acquired, trimmed, placed over and conformed to the defect, and then fully wetted with blood available in the vicinity of the defect site. Approximately 1.5 minutes after completion of wetting, the gingival flaps were then sutured to cover both the placed membrane and the defect site. After approximately 15 minutes, the flaps were reopened and the membrane evaluated for retention of its configuration. Observations showed that the material had slipped from the location of its original placement, but the material had solidified following the bony contours upon which it had settled.

The subject canine was then euthanized through an overdose of the barbituate sodium phenobarbitol. Both the treated samples and untreated controls were then evaluated utilizing the DSC scanning method of Example 2 with the exception of ice bath cooling that resulted in a scanning range between 30° C. and 250° C. to yield the following thermal features:

| | Implant Water Immersed (RB12-18) | | | | | |
|---|---|---|---|---|---|---|
| | $T_g/T_{odt}$ | $T_g/T_{odt}$ Capacity | Exotherm Peak | Exotherm Enthalpy | Melt Peak | Melt Enthalpy |
| Untreated Control | off scale | off scale | 68.2° C. | −30.6 J/g | 210.0° C. | 59.1 J/g |
| Treated Specimen | off scale | off scale | not detected | not detected | 211.5° C. | 51.5 J/g |

| | Acetone administered ex situ (RB12-28) | | | | | |
|---|---|---|---|---|---|---|
| | $T_g/T_{odt}$ | $T_g/T_{odt}$ Capacity | Exotherm Peak | Exotherm Enthalpy | Melt Peak | Melt Enthalpy |
| Untreated Control | off scale | off scale | 65.2° C. | −26.5 J/g | 210.2° C. | 60.8 J/g |
| Treated Specimen | off scale | off scale | not detected | not detected | 212.4 0C | 52.5 J/g |

| | Water administered in situ (R812-23) | | | | | |
|---|---|---|---|---|---|---|
| | $T_g/T_{odt}$ | $T_g/T_{odt}$ Capacity | Exotherm Peak | Exotherm Enthalpy | Melt Peak | Melt Enthalpy |
| Untreated Control | off scale | off scale | 66.7° C. | −29.0 J/g | 210.4° C. | 60.7 J/g |
| Treated Specimen | off scale | off scale | not detected | not detected | 212.5° C. | 57.4 J/g |

| | Water administered ex situ (RB12-31) | | | | | |
|---|---|---|---|---|---|---|
| | $T_g/T_{odt}$ | $T_g/T_{odt}$ Capacity | Exotherm Peak | Exotherm Enthalpy | Melt Peak | Melt Enthalpy |
| Untreated Control | off scale | off scale | 65.1° C. | −27.2 J/g | 209.8° C. | 61.0 J/g |
| Treated Specimen | off scale | off scale | 59.5° C. | −4.8 J/g | 212.1° C. | 54.8 J/g |

| | $T_g/T_{odt}$ | $T_g/T_{odt}$ Capacity | Exotherm Peak | Exotherm Enthalpy | Melt Peak | Melt Enthalpy |
|---|---|---|---|---|---|---|
| | | Blood administered in situ (RB12-34) | | | | |
| Untreated Control | off scale | off scale | 66.2° C. | −26.5 J/g | 210.3° C. | 61.1 J/g |
| Treated Specimen | off scale | off scale | not detected | not detected | 212.4° C. | 43.6 J/g |

By virtue of the consistent reduction in the enthalpy of the crystallization exotherm for treated web samples, substantial crystallization can be observed to have resulted from administration of the respective treatment fluid.

Example 7
PGA 50% :TMC 50% Diblock Synthesis

A reaction vessel was acquired and prepared as described in Example 4. The reaction kettle was preheated to 175° C. under nitrogen. Into the kettle, trimethylene carbonate (BI Chemicals, as received, 120.50 g) was charged with dodecyl alcohol (Kodak, as received, 0.580 g) and SnCl2.2H$_2$O (Aldrich, as received, 0.020 g). The melted mixture was stirred at 175° C. under nitrogen with a moderate stirring speed. These conditions provided adequate heat to ensure sufficiently low melt viscosity for mixing. Polymerization took place in 15 minutes shown by observing an increase in viscosity. After a total reaction time of 30 minutes, Glycolide (BI Chemicals, as received, 100.00 g) was added and the temperature was then set at 210° C. Polymerization was observed to have substantially progressed over 15 minutes as determined by an observable increase in melt viscosity. More glycolide (BI Chemicals, as received, 114.15 g) was added. Over 15 minutes, viscosity of the melt was again observed to increase. Temperature was then set at 220° C. and the high viscous melted polymer was stirred under nitrogen for another 45 minutes. During this 45 minute time period, the temperature fluctuated between 220° C. −235° C.

The polymer was discharged and cooled down to room temperature. The light brown polymer was then packaged in a medical grade plastic bag.

Example 8
Web Extrusion of Example 7 Copolymer

Utilizing the same extrusion equipment as described in Example 4b, the PGA:TMC synthesized in Example 7 was granulated and then vacuum dried for 13 hours at 130° C. The polymer was placed in the extruder with the barrel and spinneret preheated to 210° C. The polymer was then allowed to melt in the barrel for a period of 30 minutes prior to start of the extrusion process. The Transvector® was placed directly below the die face at a distance of 2.54 cm (1 inch) from the face to the top of the Transvector inlet. Compressed air was supplied to the air inlet of the Transvector at a pressure of 0.24 MPa (35 psig). Hydraulic pressure of 1.38 MPa (200 psi) was applied to the ram to force the polymer through the spinneret and the collector belt was turned on. This caused the fibers attenuated by the force of the Transvector air velocity to randomly form a continuous web of approximately 5.08 cm (2 inches) in width. The individual fibers formed cohesive bonds at contact points producing a self-cohering web.

The mean filament diameter for ten samples was measured at 33.25 microns. 2 cm ×3 cm rectangles cut from the web were found to have a mean area density of 33.57 mg/cm$^2$ (335.7 g/ m$^2$) with a standard deviation of 3.11.

Example 9
50% PGA:TMC Acquisition & Evaluation

A 50%PGA:50% TMC diblock copolymer was obtained from Birmingham Polymers (Birmingham, Ala., USA). Composition values resulting from NMR analysis revealed this copolymer to possess a 50.2% PGA:49.8% TMC ratio by weight. The inherent viscosity of the copolymer, was reported to be 0.84 dl/g in HFIP @30° C. at a concentration of approximately 0.5 g/dl.

The received copolymer was thermally evaluated by DSC in a manner similar to that described within Example 2. The obtained results are as follows:

| | $T_g$ | $T_g$ Capacity | Exotherm Peak | Exotherm Enthalpy | Melt Peak | Melt Enthalpy |
|---|---|---|---|---|---|---|
| Heat 1 | −12.4°C. | 0.27 J/g-° C. | not detected | not detected | 210.3° C. | 42.2 J/g |
| Heat 2 | 4.0°C. | 0.51 J/g-° C. | 106.3° C. | −27.8 J/g | 209.5° C. | 39.8 J/g |
| Heat 3 | 4.0°C. | 0.51 J/g-° C. | 108.0° C. | −25.8 J/g | 202.2° C. | 31.9 J/g |

Gel permeation Chromatography (GPC), also known as size exclusion chromatography (SEC), was undertaken on the copolymer resin in HFIP solvent at 40° C. and utilizing polymethyl methacrylate reference standards. The copolymer was found to possess a number averaged molecular weight ($M_N$) of 37,100 daltons and a weight averaged molecular weight ($M_W$) of 74,600 daltons which resulted in a polydispersity index ($M_N/M_W$) of 2.01.

Example 10
Web Extrusions with Example 9 Copolymer

Utilizing the 50% PGA:50% TMC (w/w) diblock copolymer lot described within Example 9, extrusion was undertaken utilizing parameters similar to that described in Example 1 except that extruder temperatures were set to produce a spin pack or die temperature of 215° C. and two groups of web were created utilizing differing belt speeds. Both groups produced tactilely supple cohesive webs possessing a center thickness of approximately 0.15 cm (0.06 inches) that were then pressed and then oven conditioned at 75° C. for 2 hours with the intention of inducing microphase separation and crystallization.

The two produced webs possessed an average fiber diameter of 56 micrometers with a standard deviation of approximately 5 micrometers, and possessed average thicknesses of 0.86 (0.034 inches) and 0.99 mm (0.039 inches). Coverage or area density was found to average 56 mg/cm$^2$ (560 g/m$^2$) for the thinner sample and 75.4 mg/cm$^2$ (754 g/m$^2$) for the thicker web while the average apparent density for the finished samples ranged from 0.65 g/cc to 0.76 g/cc. The web was tensile tested after conditioning at 37° C. in saline solution for 1 hour and found to possess a maximum tensile stress of 0.56 kg/mm$^2$ (5.5 MPa) while the web's IV was found to be approximately 0.8 dl/g in both samples.

Example 11
Placement of Example 10 Copolymer into Mandible of a Rat

The material produced within Example 10 was cut into twelve 2 cm x2.5 cm pieces and divided into two groups with differing average thicknesses. Based on acquired data, the thinner pieces were projected to possess a representative Gurley Stiffness of approximately 976 mg, while the thicker pieces possessed an estimated 1850 mg of Gurley stiffness. Each piece was individually sealed within moisture proof packaging and gamma sterilized at 15 kGy.

The described material was then evaluated for its ability to regenerate bone within the rat mandible model. A full discussion of this particularly severe animal model is contained within the following references that describe in detail the methodology, evaluation, and relative performance of other biomaterials and implant structures:

Zellin E, Gritli-Linde A, Linde A. Healing of mandibular defects with different biodegradable and non-biodegradable membranes: an experimental study in rats. *Biomaterials* 1995; 16:601–609.

Sandberg E, Dahlin C, Linde A. Bone regeneration by osteopromotion technique using bioabsorbable membranes: An experimental study in rats. *Journal of Oral & Maxillofacial Surgery* 1993; 51(10):1106–1114.

The dimensions of the actual implanted web varied dependent on the site and the discretion of the surgeon.

Postoperative healing was uneventful. Upon retrieval and histological sectioning after 4 weeks in vivo, it was found that both thicknesses of the web showed no collapse at all into the defect. However, ingrowth of soft tissue was frequently observed at the antero-lingual aspect of the mandible providing indication of excessive stiffness with poor adaptation of the web to the contours of the defect. All the tested membranes maintained sufficient space to produce new bone and showed no signs of collapse.

The surfaces and interstices of the material were populated with some inflammatory cells and multinucleated giant cells along with fibrous tissue and some intermittent ingrowth of bone.

Example 12
Web formed into Tube Configuration

Web was formed from 50% PGA:50% TMC copolymer similar to that described in Example 9 and processed in a manner similar to that described in Example 1. The produced web was observed to be "tacky" enough to adhere to itself. The web was compressed under 0.14 MPa (20 psi) pressure to reduce porosity and then cut into rectangles of 2.25 cm by 1.75 cm. These supple specimens were then rolled around a 4 mm stainless steel mandrel creating a tube with an overlapping seam. This seam was then pressed together using moderate finger pressure allowing the membrane to bond at this point. The membranes and mandrels were then placed in an oven, preheated to 70° C., for one hour; once removed from the oven, the tubes were taken from the mandrel, and stored for packaging. When the resulting seam bond of a selected sample was challenged with tweezers, it appeared to have strength similar to that of the starting web. The remaining tubes were then desiccated inside a foil/polymer pouch at 65° C. for 17 to 24 hours prior to sealing. The packages were then gamma irradiated at a dose level of 15 kGy.

Example 13
Tubular Web from Example 12 Use in Tibia of a Rabbit

A study was conducted, using a rabbit forelimb model, to evaluate the effects of the PGA: TMC tubes provided by Example 12 on the regeneration of bone in segmental, long-bone defects. The PGA: TMC tubes were thought to provide a temporary mechanical barrier around the long-bone defect, preventing connective tissue and undifferentiated fibroblasts from filling the defect area while providing a scaffold for new bone (a kind of template to contour and shape newly formed bone). Although speculative, the tubes could also concentrate cellular and molecular factors required for healing (i.e., excluding cell-derived inhibitory factors and concentrating local growth factors).

Adult, 11 kg (5 pound) to 22 kg (10 pound) New Zealand white female rabbits were used in the study. 10 mm defects (full thickness osteotomies) were created in the diaphyseal portion of the radius; this size defect is known to produce nonunions in rabbits, if left untreated. A dorso-medial incision was made along the length of the radius; the extensor carpi radialis musculature was elevated from the radius and reflected laterally to expose the mid-shaft of the radius. Two full thickness cuts were made (chilled sterile saline was used to irrigated the area to prevent thermal necrosis during cutting), 10 mm apart, in the diaphyseal portion of the radius just proximal to the tendon insertion of pronator teres. Taking care not to disrupt the interosseous membrane between the radius and ulna any more than necessary (the membrane provides stability for the defect; a kind of natural internal splint), the cut bone block was removed, the periosteum was removed from the cut bone ends, and a 10 mm defect was left.

PGA: TMC tubes were positioned over the 10 mm defects. The tubes were slipped onto the proximal end of the radius first, and then trimmed, if necessary, and placed over the distal bone end. The tubes were made to fit snugly over the bone ends, overlapping the bone by 2 to 3 mm; the tubes did not require sutures to hold them in place.

Animals were followed, in life, for approximately 6 months. Radiographs were taken at 2, 3, 4, 5, and 6 months postoperatively, using a Siemans, Heliodent 70 x-ray machine with dental cone attachment. Radiographs were taken using Kodak Ultra-speed film, at an exposure time of 0.20 ms. Radiographs provided a relatively simple, noninvasive assessment of the efficacy of treatment. Radiodense areas of apparent new bone were noted at 2 months postoperative in the series treated with PGA: TMC tubes. Controls (10 mm defects left untreated) showed little bone formation throughout the 6 month study, and resulted in fibrous nonunions. Apparent cortical bone in the treated group densified over the six month treatment period; in some cases, the new bone bridged the defect gap and in all cases the amount of newly formed bone reduced the defect gap.

The observation could be made that the defects treated with PGA: TMC tubes demonstrated a significant degree of bone healing over a period of six months, and in some cases bone fully bridged the defect gap.

Example 14
Three-dimensional Web Construction

Utilizing similar polymer and extrusion conditions as that described within Example 1, a substantially thicker self-cohering web was produced by reversing the direction of the take-up belt after deposition of a 25.4 cm to 30.5 cm linear segment of web. This fabrication approach, conducted at a belt distance of 120.7 cm from the bottom of the Transvector, provided for the sequential deposition of a new web layer atop of any previously deposited web layer or layers. As a result of numerous repetitions of this layering oscillation, a self-cohesive web was able to be produced which possessed at its midsection an approximately 5.2 cm web thickness. The produced cohesive web was then removed from the belt as a single unit and compressed to a 1.9 cm thickness under the weight of a plate spanning two 1.91 cm thick spacers. The assembly and web was then subjected to 70° C. heat for 2 hours. The resulting 1.8 cm thick cohesive web was found to have fibers ranging from 27 to 55 micron in diameter with an average of diameter of 44.5 microns along with an inherent viscosity of 0.85 dl/g. A section sampled from the central region of the compressed web was found to possess an apparent density of approximately 0.3 g/cm$^3$. The produced self-cohering web was found to have no requirement for calendaring to achieve a cohesive interfiber bonding and upon moderate handling to be resistant to fiber separation without the addition of binders and was easily trimmed or contoured with a standard or curved scissors to any dimension smaller than that of the web.

Example 15
Blend of Equal Parts PGA Homopolymer and 50:50 triblock PGA:TMC Copolymer.

A 4CV Helicone Mixer (Design Integrated Technologies, Warrenton, Va., USA) located within a Class 10,000 clean room and connected to a Sterling brand hot oil system (Model #S9016, Sterling, Inc., Milwaukee, Wis., USA) able to maintain temperatures up to 230° C. was pre-cleaned to remove any polymeric or other residues and then thoroughly air dried for 2 hours before reattachment of the mixer bowl. The dry mixer was then preheated to 140° C. followed by a purge and then blanketing with anhydrous nitrogen a minimum flow during the course of the experiment. A foil package containing 740.7 grams of trimethylene carbonate was opened and the contents introduced followed by mixing at a speed setting of "6.5". After 10 minutes stirring was stopped and 2.73 grams of a combination of 0.228 grams of SnCl2.2H$_2$O catalyst and 15.71 grams of diethylene glycol initiator was then added directly to the melted TMC. Mixing was recommended and after 10 minutes the temperature was raised to 160° C. which was then followed by an increase to 180° C. after 30 minutes. After an additional 30 minutes, 75 grams of glycolide monomer was added followed by an increase of the temperature to 200° C. After 15 minutes then 675 grams of glycolide were added and the temperature setting immediately raised to 220° C. After 40 minutes the polymerized product was discharged at the 220° C. onto a clean release surface where it solidified as it cooled down to room temperature. The light brown polymer that was obtained was then packaged in a pyrogen free plastic bag and then mechanically granulated through 4.0 mm screen prior to further analysis and processing.

Approximately 500 grams each of this 50% PGA:50% TMC triblock copolymer, which was found to possess an inherent viscosity of 0.99 dl/g, and PGA homopolymer (inherent viscosity 1.75 dl/g–Birmingham Polymers Lot # D-96156) were placed into a vacuum oven, heated for 1 hour at 130° C., and then placed under a vacuum of approximately 736 torr that was maintained for a minimum of 15 hours along with the continued application of heat.

A Brabender Prep Mixer equipped with roller blades and a Brabender Plast-Corder PL2000 and Mixer Measuring Head (available from C. W. Brabender Instruments, Inc., South Hackensaack, N.J., USA) was preheated to 235° C. and the mixing blades had been actuated to the desired speed of 50 rpm. 128 grams of the PGA homopolymer and 128 grams of the PGA:TMC triblock copolymer were then added and a nitrogen line was placed at the feed opening of mixer to prevent moisture uptake by the polymer. The temperature of the melt and torque of the mixer were monitored on the graphics screen. Visual inspection of the blend at 5 minutes indicated that the polymer was melting well and again began to have the appearance of taffy. After a total mixing time of 13 minutes the torque flattened out, the polymer was removed and the machine cleaned. A printout was made of the graphics screen which indicated the torque had indeed stabilized. The solidified blended polymer was then mechanically granulated through a 4 mm screen prior to further analysis and processing.

Resin Characterization

Granules from produced blend were found to possess an inherent viscosity of 1.06 dL/g when evaluated in a manner similar to that described in Example 1. DSC evaluation resulted in detection of a very weak $T_g$ and the following summary results:

|  | $T_g$/Todt | $T_g$/Todt Capacity | Exotherm Peak | Exotherm Enthalpy | Melt Peak | Melt Enthalpy |
|---|---|---|---|---|---|---|
| Heat 1 | 0.0° C. | 0.16 J/g*° C. | none | none | 221° C. | 51.0 J/g |

Web Processing & Characterization

The prepared blend was able to produce a self-cohering web utilizing a die pack temperature of 238° C. in combination with extrusion conditions similar to that described in Example 1 above.

The web produced from the blended polymers possessed an IV of 1.06 dl/g when evaluated in a manner as described in Example 1. A DSC of the produced web using parameters as described in Example 2 revealed the following thermal characteristics:

|  | $T_g$/Todt | $T_g$/T$_{odt}$ Capacity | Exotherm Peak | Exotherm Enthalpy | Melt Peak | Melt Enthalpy |
|---|---|---|---|---|---|---|
| Heat 1 | 24.0° C. | 0.75 J/g*° C. | 67.3° C. | −31.4 J/g | 218° C. | 64.0 J/g |
| Heat 2 | 8.2° C. | 0.22 J/g*° C. | none | none | 216.5° C. | 52.7 J/g |
| Heat 3 | 4.4° C. | 0.25 J/g*° C. | none | none | 214.5° C. | 52.6 J/g |

Example 16

Webs from PHB:PHV Resins

Biopol™ brand poly-B-hydroxybutyrate-hydroxyvalerate (PHB:PHV) "low" valerate content D310G and "high" valerate D610G plasticized copolymers were acquired from Zeneca Pharmaceuticals (Wilmington, Del.). The manufacturer did not provide either the specific copolymer ratios or the identify of the utilized plasticizer.

Approximately 10 mg of the D310G copolymer was placed into an aluminum DSC sample pan, covered, and analyzed utilizing a Perkin-Elmer DSC 7 equipped with an Intracooler II cooling unit able to provide sample cooling to temperatures as low as −40° C. The sample was scanned from −40° C. to 180° C. at a scanning rate of 10° C./min. After completion of this initial scan, the sample was immediately cooled at the maximum rate provided by the instrument (−500° C./min setting). A second similar scan was undertaken on the same sample over the same temperature range. After scan completion and thermal maintenance at 180° C. for 5 minutes, the sample was again cooled at the maximum rate provided by the instrument and a third scan undertaken.

Each scan was analyzed for the observed inflection point $T_g$, $T_{odt}$, crystallization exotherm, and melt endotherm. The results are summarized in the following table.

|  | $T_g/T_{odt}$ | $T_g/T_{odt}$ Capacity | Exotherm Peak | Exotherm Enthalpy | Melt Peak | Melt Enthalpy |
|---|---|---|---|---|---|---|
| Heat 1 | not detected | not detected | none | none | 166.0° C. | 81.4 J/g |
| Heat 2 | 0.0° C. | 0.28 J/g*° C. | none | none | 161.2° C. | 78.4 J/g |
| Heat 3 | 0.2° C. | 0.36 J/g*° C. | none | none | 160.4° C. | 79.5 J/g |

Similarly, the D610G high valerate content polymer was DSC scanned for the observed inflection point $T_g$, $T_{odt}$, crystallization exotherm, and melt endotherm. The results, which included an additional peak at approximately 145° C. which provided a doublet melt peak for the second and third scans are summarized in the following table.

|  | $T_g/T_{odt}$ | $T_g/T_{odt}$ Capacity | Exotherm Peak | Exotherm Enthalpy | Melt Peak | Melt Enthalpy |
|---|---|---|---|---|---|---|
| Heat 1 | not detected | not detected | none | none | 158.7° C. | 64.8 J/g |
| Heat 2 | −12.8° C. | 0.31 J/g*° C. | none | none | 159.0° C. | 55.0 J/g |
| Heat 3 | −8.1° C. | 0.28 J/g*° C. | none | none | 159.9° C. | 55.8 J/g |

Approximately 100 grams of the as delivered pelletized D310G copolymer was heated for 2.5 hours under vacuum at 105° C. Upon completion, the vacuum dried polymer was then allowed to feed into the extruder system described in Example 1 and ultimately heated to 184° C. and extruded using an accompanying Transvector pressure of 0.17 MPa (25 psi).

After greater than 10 seconds of cooling at ambient temperature, the produced web was removed from the fabric belt and examined. The retrieved article was found to be a tactilely supple cohesive fibrous web where individual component fibers did not appear to fray or separate from the web when subjected to moderate handling.

Similarly, the higher PHV content D610G polymer was extruded at 190° C. an 32 psi (221 kPa) Transvector pressure. Extrusion of this polymer also resulted in a self-cohering fibrous web that was found to initially be tactilely supple where individual component fibers did not appear to fray or separate from the web when subjected to moderate handling. Both of the produced webs were found to become significantly stiffer after a few minutes at room temperatures.

Example 17

Attempted Self-cohering Web from PDS Homopolymer

Acquisition/Characterization Polydioxanone polymer (Lot #76013) was obtained from BI Chemicals, Inc., Petersburg, Va., USA. Characterization of the supplied resin was undertaken utilizing DSC in a manner similar to that described in Example 1. The results of the three DSC scans are as follows:

|  | $T_g/T_{odt}$ | $T_g/T_{odt}$ Capacity | Exotherm Peak | Exotherm Enthalpy | Melt Peak | Melt Enthalpy |
|---|---|---|---|---|---|---|
| Heat 1 | −10.5° C. | 0.20 J/g*° C. | none | none | 111.7° C. | 87.5 J/g |
| Heat 2 | −13.3° C. | 0.70 J/g*° C. | 44.9° C. | −48.4 J/g | 103.4° C. | 51.7 J/g |
| Heat 3 | −27.8° C. | 0.64 J/g*° C. | 43.5° C. | −35.4 J/g | 97.9° C. | 44.5 J/g |

The resulting DSC thermograms revealed that quenching could be achieved with this polymer system as evidenced by the cold crystallization exotherm occurring between the $T_g$ and the $T_m$ in both the second and third heatings. The observed inflection point temperature of −13.3° C. for the quenched $T_g$ was observed to possess reasonable agreement with the $T_g$ of −16° C. reported for poly-p-dioxanone in U.S. Pat. No. 4,052,988. Since the tested poly-p-dioxanone material is a homopolymer, a shift of the $T_g$ toward an order-disorder transition reflective of a mixing with another polymer system was not expected and could not be observed.

Extrusion

The polymer was processed utilizing the apparatus and general conditions described in Example 1 above except that the undried polymer was extruded at a screw speed of 20–25 and a melt temperature of 156° C., with the temperature later increased to 161° C. As in earlier examples, the resulting fibrous web that accumulated on the belt possessed a relatively consistent loft along the direction of belt movement, while the amount of accumulated fibers diminished in height on either side of the centerline when observing in line with the direction of belt movement.

After greater than 10 seconds of cooling at ambient temperature, the web was removed from the fabric belt and examined. It was found that the individual fibers of web which accumulated on the take up screen at the lower extrusion temperature were not observed to adhere to themselves. If any interfiber adherence was notable, minimal tension loading applied to those fibers resulted with rupture of the developed interfiber bonds and their respective separation from the bulk of the web. Similar poor interfiber adhesion was observed when room temperature Transvector air was applied to the system. Despite an extruder die temperature increase to 161 ° C., little impact on the formation of a cohesive fibrous web could be observed.

The only observed conditions which were found to allow bonding of individual fibers and any observable web cohesion occurred only if the Transvector air flow was removed and the fibers allowed to accumulate on the belt and cool under ambient conditions. These slow cooling conditions, the result of processing temperatures approximately 50° C. above the polymer's melt point combined with the relatively slow cooling rate afforded by the larger diameter fibers, produced sufficient duration of the melt to produce a cohesive web of large diameter fibers ranging from 236 μm to 330 μm in diameter. This contrasts with the 15 to 50 μm diameter fibers produced with various other copolymers and polymeric blends described herein. The weaker bonding that resulted with these large diameter fibers was believed indicative that cohesive interfiber bonding observed in this example was the result of a prolongation of the melt state rather than through contact of fibers in a disordered amorphous state that is believed to produce the superior interfiber bonding that is reported in other examples.

Example 18

60%:40% (w/w) Blend of Poly(p-dioxanone) and PGA Homopolymer

Utilizing a Brabender Prep Mixer preheated to 235° C. and method described within is Example 15 above, a 60% (w/w) mixture of poly(p-dioxanone) homopolymer and 40% poly(glycolide) was prepared by blending 100 grams of PGA homopolymer (Inherent Viscosity 1.59 dL/g—Birmingham Polymers Lot # D97069) and 150 grams of poly(p-dioxanone) homopolymer (Inherent Viscosity 2.31 dL/g Boehringer Ingelheim lot # 76013) for 16.5 minutes beyond the point when the mixer's torque flattened out. The polymer was then removed, allowed to solidify, and then mechanically granulated through a 4 mm screen prior to further analysis and processing.

DSC evaluation of granules from produced blend resulted in detection of a $T_g$ and the following summary results:

|  | $T_g$/Todt | $T_g$/Todt Capacity | Exotherm Peak | Exotherm Enthalpy | 1st Melt Peak | 1st Melt Enthalpy | 2nd Melt Peak | 2nd Melt Enthalpy |
| --- | --- | --- | --- | --- | --- | --- | --- | --- |
| Heat 1 | −20.0° C. | 0.19 J/g*° C. | none | none | 91° C. | 32.0 J/g | 224° C. | 37.0 J/g |

The prepared blend was used to produce a web utilizing a die pack temperature of 193° C. in combination with general extrusion conditions similar to that described in Example 1 above.

The self-cohering web that was able to be produced from the blended polymers possessed an IV of 0.63 dl/g when evaluated in a manner as described in Example 1. A DSC of the produced web using parameters as described in Example 2 revealed the following thermal characteristics:

|  | $T_g$/Todt | $T_g$/Todt Capacity | Exotherm Peak | Exotherm Enthalpy | 1st Melt Peak | 1st Melt Enthalpy | 2nd Melt Peak | 2nd Melt Enthalpy |
| --- | --- | --- | --- | --- | --- | --- | --- | --- |
| Heat 1 | −15.8° C. | 0.73 J/g*° C. | 38.7° C. | −35.4 J/g | 96.0° C. | 28.6 J/g | 221.7° C. | 48.3 J/g |
| Heat 2 | −22.8° C. | 0.38 J/g*° C. | 13.7° C. | −11.6 J/g | 99.9° C. | 36.4 J/g | 205.7° C. | n/a |
| Heat 3 | −27.1° C. | 0.12 J/g*° C. | 12.5° C. | −8.8 J/g | 93.7° C. | 26.6 J/g | 209.0° C. | 39.6 J/g |

The observed presence of two crystalline endothermic melt peaks at temperatures reflective of the respective homopolymers provide evidence of two distinct phase separated crystalline phases within the produced self-cohesive fibrous web.

Example 19

Lap Shear Evaluation of Non-woven Webs

Lap shear testing was conducted utilizing the general methodology described within ASTM Method D3164-92A, "Standard Test Method for Strength Properties of Adhesively Bonded Plastic Lap-Shear Sandwich Joints in Shear by Tensile Loading", on a series of non-woven web samples formed from extrusion based web forming processes and compiled by the INDA, Association of the Non-woven Fabrics Industry (Cary, N.C., USA) and made available through its third edition of the Non-woven Fabrics Sampler (1992). Also, evaluated utilizing the same test methodology was a DuPont Tyvek® 1073B spunbonded olefin web utilized as a porous lid for steam sterilizable packaging (available in a variety of dimensions from Oliver Products, Grand Rapids, Mich., USA). Additionally evaluated was the implantable bioresorbable non-woven product Resolut® Regenerative Material available from W. L. Gore & Associates, Flagstaff, Ariz., USA.

In order to provide for web cohesion within the small sample sizes available in the implantable bioresorbable Resolut® non-woven material, the ASTM test dimension was both selected and modified to accommodate a specimen size of approximately 12.5 mm (0.5 inches) by 12.5 mm (0.5 inches). Each specimen was mounted onto the adhesive side of a larger section of double-sided indoor/outdoor fiberglass reinforced carpet tape (stock #10-2 available from Manco, Inc., Avon, Ohio, USA) which was then precisely trimmed with scissors to minimize exposure of adhesive outside of the planar boundaries of the mounted specimen. The opposing side of each web specimen was then affixed to the adhesive side of a similar tape section which was then also trimmed to the boundaries of the web sample. The removable tape backing was detached from one side of the adhesive-web-adhesive laminate and the exposed adhesive surface made available to affix to a wooden tongue depressor of approximately 1.75 cm in width and 15 cm in length. Once the specimen was centered across the width of the depressor at a point approximately 2 cm from one end, ample finger pressure was then applied. The remaining backing was then removed and the adhesive surface affixed to a similar location on the surface of another wooden tongue depressor in a planar orientation 180° to that of the first depressor in order to provide for tensile shear loading of the overlapping areas joined solely with the web structure.

Precautions were undertaken to evaluate webs which possessed sufficient loft or density to assure that direct contact of the two adhesive surfaces did not occur through the plane of the web specimen. Generally, samples which were equal to or less than 0.1 mm (0.004 inches) thick and possessed a volume density of less than 0.2 g/ cm$^2$ were not evaluated based on the proximity of their opposing surfaces, the relatively large size of interfiber distances, and the related risk for adhesive-to-adhesive contact. In marginal samples, finger pressure was applied only as needed to induce cohesive failure within the test samples and therefore minimize risk of adhesive layers contacting.

No special adhesive preparation precautions were found to be necessary to induce most test samples into undergoing a cohesive failure within the web specimen. However, stronger samples such as those of the current invention where significantly high web cohesive strength induces increased potential for adhesive failure with either the web or wooden surfaces required additional adhesive surface preparations commonly known to those skilled in the art to induce a cohesive failure mode within the web specimen. Such preparations could include the use of light abrasion of the web itself, the abrasion of the wooden adhesive surface, the application of pressure to the joined materials. In all accepted test results such preparations were utilized as needed to induce a valid cohesive failure within the web specimen. All results which induced adhesive failures at either the web or depressor interface were rejected as invalid along with any cohesive failures observed to occur within the boundaries of the adhesive itself.

The results of tensile loading of the specimens described above at a strain rate of 250 mm/minute are contained in the following chart which also includes a brief description of each sample type.

Nonwoven Web Lap Shear Strength Survey Results

| Sample | Weight (mg) | Thickness (inches) | Thickness (mm) | Area Density (g/m2) | Density (mg/cm3) | Max Load (N) | Shear Stress (MPa) |
|---|---|---|---|---|---|---|---|
| Web from | 124 | 0.065 | 1.65 | 939 | 569 | 143 | 1.08 |
| Example #10 | 126.3 | 0.067 | 1.70 | 915 | 538 | 150 | 1.08 |
|  | 106.9 | 0.057 | 1.45 | 808 | 558 | 144 | 1.09 |
|  | 73.22 | 0.035 | 0.89 | 469 | 528 | 194 | 1.24 |
|  | 62.56 | 0.034 | 0.86 | 473 | 548 | 185 | 1.40 |
| 1073B Tyvek | 10.75 | 0.006 | 0.15 | 66 | 434 | 113 | 0.69 |
| Spunbond | 11.25 | 0.007 | 0.18 | 71 | 397 | 69 | 0.43 |
| INDA #E1 | 5.7 | 0.005 | 0.13 | 37 | 288 | 36 | 0.23 |
| Polyethylene | 6.16 | 0.005 | 0.13 | 39 | 305 | 44 | 0.28 |
| Flashspun | 6.08 | 0.005 | 0.13 | 42 | 332 | 40 | 0.28 |
| INDA #E2 | 10.62 | 0.009 | 0.23 | 63 | 277 | 69 | 0.41 |
| Polypropylene |  |  | 0.00 |  |  |  |  |
| Spunbond |  |  | 0.00 |  |  |  |  |
| INDA #E5 | 14.09 | 0.011 | 0.28 | 92 | 329 | 108 | 0.71 |
| Polyester | 15.19 | 0.011 | 0.28 | 97 | 348 | 45 | 0.29 |
| Spunbond | 17.19 | 0.011 | 0.28 | 98 | 352 | 109 | 0.62 |
| INDA #E6 | 37.04 | 0.039 | 0.99 | 247 | 249 | 107 | 0.71 |
| Polyester | 32.72 | 0.035 | 0.89 | 209 | 236 | 101 | 0.65 |
| Spunbond | 30.06 | 0.036 | 0.91 | 196 | 215 | 97 | 0.63 |
| INDA #E7 | 15.35 | 0.012 | 0.30 | 98 | 322 | 57 | 0.36 |
| Polyester | 14.13 | 0.013 | 0.33 | 89 | 269 | 63 | 0.40 |
| Spunbond | 10.54 | 0.009 | 0.23 | 62 | 273 | 74 | 0.44 |
| INDA #E9 | 4.49 | 0.005 | 0.13 | 28 | 222 | 10 | 0.06 |
| Meltblown | 5.59 | 0.006 | 0.15 | 30 | 194 | 14 | 0.07 |
| Polypropylene | 4.06 | 0.005 | 0.13 | 28 | 218 | 7 | 0.05 |
| INDA #E13 | 13.88 | 0.013 | 0.33 | 91 | 275 | 63 | 0.41 |
| Spunlaid | 14.79 | 0.014 | 0.36 | 93 | 261 | 63 | 0.40 |
| Bicomponent | 15.89 | 0.015 | 0.38 | 102 | 267 | 54 | 0.34 |

-continued

Nonwoven Web Lap Shear Strength Survey Results

| Sample | Weight (mg) | Thickness (inches) | Thickness (mm) | Area Density (g/m2) | Density (mg/cm3) | Max Load (N) | Shear Stress (MPa) |
|---|---|---|---|---|---|---|---|
| Resolut | 18.92 | 0.014 | 0.36 | 124 | 348 | 88 | 0.57 |
| R6 Configuration | 20.73 | 0.014 | 0.36 | 144 | 405 | 71 | 0.50 |
| Lot R197A01 | 23.69 | 0.014 | 0.36 | 152 | 427 | 73 | 0.47 |

Thus, article of the present invention comprises a continuous filament non-woven web which possesses, without requiring added adhesive binders or adjuncts, or post-extrusion melt processing a cohesive shear strength exceeding 0.8 MPa when tension loaded as a lap-shear sandwich joint (tested as described above). It likewise can be provided in forms having these shear strength values in excess of 1.0, 1.2 and 1.4 MPa. This article can also be provided in bioresorbable form (also without requiring added adhesives binders or adjuncts or post-extrusion melt processing) with this shear strength in excess of 0.6 MPa as well as in excess of the same values for the above-described article to which is not bioresorbable.

What is claimed is:

1. An article comprising melt-formed continuous filaments intermingled to form a porous web wherein said filaments are self-cohered to each other at multiple contact points, wherein said filaments comprise at least one semi-crystalline polymeric component covalently bonded to or blended with at least one amorphous polymeric component, and wherein the filaments possess partial to full polymeric component phase immiscibility when in a crystalline state.

2. An article according to claim 1 wherein the at least one semi-crystalline polymeric component is covalently bonded to the at least one amorphous polymeric component.

3. An article according to claim 2 wherein the components comprise a block copolymer.

4. An article according to claim 1 wherein the at least one semi-crystalline polymeric component is blended with the at least one amorphous polymeric component.

5. An article according to claim 4 wherein at least one of the components is a block copolymer.

6. The article of claim 1 comprising an implantable article.

7. The article of claim 6 which is proportioned for guided tissue regeneration.

8. The article of claim 1 wherein at least one semi-crystalline polymeric component has a melting point of greater than 80° C.

9. The article of claim 1 wherein the web has a density of greater than 120 g/m2.

10. The article of claim 1 wherein the web is bioresorbable.

11. The article of claim 10 wherein the web has single bioresorption time.

12. The article of claim 1 wherein the web is a shaped form.

13. An article of claim 1 wherein said article incorporates at least one bioactive agent with the filaments of the web.

14. An article of claim 13 wherein said at least one bioactive agent is selected from the group consisting of osteoconductive substances, osteoinductive substances, growth factors, chemotactic factors, morphogens, pharmaceuticals, proteins, peptides and biologically active molecules of autogenic, allogenic, xenogenic or recombinant origin.

15. An article of claim 13 wherein said at least one bioactive agent is selected from the group consisting of transforming growth factor beta, bone morphogenic proteins, osteogenic proteins, antibiotics, antimicrobials, vascular endothelial growth factor, basic fibroblast growth factor, platelet derived growth factor, insulin-like growth factor, insulin and immunoglobulin type G antibodies.

16. An article of claim 13 wherein said at least one bioactive agent comprises an antibiotic.

17. An article of claim 13 wherein said at least one bioactive agent comprises an antimicrobial.

18. An article of claim 1 comprising a continuous filament non-woven web wherein the web possesses, without requisite for added adhesive binders, adjuncts, or post-extrusion melt processing, cohesive shear strength exceeding 0.8 megapascals when tension loaded in shear as a lap-shear sandwich joint.

19. An article of claim 18 wherein the web possesses cohesive shear strength exceeding 1.0 megapascals when tension loaded in shear as a lap-shear sandwich joint.

20. An article of claim 18 wherein the web possesses cohesive shear strength exceeding 1.2 megapascals when tension loaded in shear as a lap-shear sandwich joint.

21. An article of claim 18 wherein the web possesses cohesive shear strength exceeding 1.4 megapascals when tension loaded in shear as a lap-shear sandwich joint.

22. An article comprising melt-formed continuous filaments intermingled to form a porous web wherein said filaments are self-cohered to each other at multiple contact points, wherein said filaments comprise a first semi-crystalline polymeric component covalently bonded to or blended with at least one additional semi-crystalline polymeric component, and wherein the filaments possess partial to full polymeric component phase immiscibility when in a crystalline state.

23. An article according to claim 22 wherein the first semi-crystalline polymeric component is covalently bonded to the at least one additional semi-crystalline component.

24. An article according to claim 23 wherein the components comprise a block copolymer.

25. An article according to claim 22 wherein the first semi-crystalline polymeric component is blended with the at least one additional semi-crystalline component.

26. An article according to claim 25 wherein at least one of the components is a block copolymer.

27. The article of claim 22 comprising an implantable article.

28. The article of claim 27 which is proportioned for guided tissue regeneration.

29. The article of claim 22 wherein at least one semi-crystalline polymeric component has a melting point of greater than 80° C.

30. The article of claim 22 wherein the web has a density of greater than 120 g/m2.

31. The article of claim 22 wherein the web is bioresorbable.

32. The article of claim 31 wherein the web has single bioresorption time.

33. The article of claim 22 wherein the web is a shaped form.

34. An article of claim 22 wherein said article incorporates at least one bioactive agent to with the filaments of the web.

35. An article of claim 34 wherein said at least one bioactive agent is selected from the group consisting of osteoconductive substances, osteoinductive substances, growth factors, chemotactic factors, living cells, morphogens, pharmaceuticals, proteins, peptides and biologically active molecules of autogenic, allogenic, xenogenic or recombinant origin.

36. An article of claim 34 wherein said at least one bioactive agent is selected from the group consisting of transforming growth factor beta, bone morphogenic proteins, osteogenic proteins, antibiotics, antimicrobials, vascular endothelial growth factor, basic fibroblast growth factor, platelet derived growth factor, insulin-like growth factor, insulin and immunoglobulin type G antibodies.

37. An article of claim 34 wherein said at least one bioactive agent comprises an antibiotic.

38. An article of claim 34 wherein said at least one bioactive agent comprises an antimicrobial.

39. An article of claim 22 comprising a continuous filament non-woven web wherein the web possesses, without requisite for added adhesive binders, adjuncts, or post-extrusion melt processing, cohesive shear strength exceeding 0.8 megapascals when tension loaded in shear as a lap-shear sandwich joint.

40. An article of claim 39 wherein the web possesses cohesive shear strength exceeding 1.0 megapascals when tension loaded in shear as a lap-shear sandwich joint.

41. An article of claim 39 wherein the web possesses cohesive shear strength exceeding 1.2 megapascals when tension loaded in shear as a lap-shear sandwich joint.

42. An article of claim 39 wherein the web possesses cohesive shear strength exceeding 1.4 megapascals when tension loaded in shear as a lap-shear sandwich joint.

* * * * *